United States Patent [19]

Yellin et al.

[11] 4,447,441
[45] May 8, 1984

[54] HALOALKYLGUANIDINE COMPOUNDS, PHARMACEUTICAL COMPOSITIONS AND METHODS, PROCESSES AND INTERMEDIATES

[75] Inventors: Tobias O. Yellin, Fremont, Calif.; David J. Gilman, Macclesfield, England

[73] Assignee: Imperial Chemical Industries PLC, London, England

[21] Appl. No.: 353,502

[22] Filed: Mar. 1, 1982

[30] Foreign Application Priority Data

Mar. 9, 1981 [GB] United Kingdom ................ 8107273
Sep. 17, 1981 [GB] United Kingdom ................ 8128179

[51] Int. Cl.$^3$ ................ C07D 231/38; C07D 249/04; A61K 31/41; A61K 31/415

[52] U.S. Cl. .................................... 424/269; 424/249; 424/251; 424/263; 424/270; 424/272; 424/273 R; 424/273 P; 544/194; 544/204; 544/317; 544/335; 544/336; 544/408; 548/185; 548/194; 548/230; 548/236; 548/255; 548/260; 548/265; 546/297; 546/306

[58] Field of Search ............... 548/375, 185, 194, 230, 548/236, 255, 260, 265; 424/269, 270, 272, 273 R, 273 P

[56] References Cited

U.S. PATENT DOCUMENTS

| | | | |
|---|---|---|---|
| 4,117,131 | 9/1978 | Schwender et al. | 424/270 |
| 4,165,377 | 8/1979 | Jones et al. | 424/270 |
| 4,165,378 | 8/1979 | Gilman et al. | 424/270 |
| 4,234,735 | 9/1980 | Jones et al. | 424/270 |
| 4,242,350 | 12/1980 | Yellin et al. | 424/270 |
| 4,242,351 | 12/1980 | Yellin et al. | 424/270 |
| 4,248,784 | 2/1981 | Bell et al. | 424/270 |
| 4,252,819 | 2/1981 | Hirata et al. | 424/270 |
| 4,262,126 | 4/1981 | Gilman et al. | 424/270 |
| 4,309,435 | 1/1982 | Yellin et al. | 424/270 |
| 4,315,009 | 2/1982 | Jones et al. | 424/270 |
| 4,332,949 | 6/1982 | Yellin et al. | 424/270 |
| 4,362,728 | 12/1982 | Yellin | 424/249 |

*Primary Examiner*—Robert Gerstl
*Attorney, Agent, or Firm*—Cushman, Darby & Cushman

[57] ABSTRACT

The invention relates to guanidine derivatives which are histamine H-2 antagonists and which inhibit gastric acid secretion. According to the invention there is provided a guanidine derivative of the formula I:-

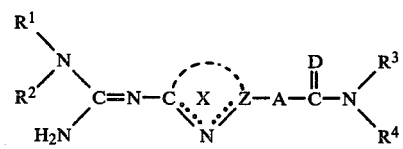

in which $R^1$ and $R^2$, same or different, are hydrogen or 1-10C alkyl, 3-8C cycloalkyl or 4-14C cycloalkylalkyl, each alkyl, cycloalkyl or cycloalkylalkyl optionally carrying one or more F, Cl or Br atoms, provided that one of $R^1$ and $R^2$ is halogen substituted, or $R^2$ is hydrogen and $R^1$ is $R^5$—E—W in which W is 2-6C alkylene optionally substituted by 1 or 2 1-4C alkyls, E is O,S or $NR^6$ in which $R^6$ is H or 1-6C alkyl, $R^5$ is H or 1-6C alkyl optionally substituted by 1 or 2 1-4C alkyls, or $R^5$ and $R^6$ are joined to form a pyrrolidine, piperidine, morpholine, piperazine or N-methylpiperazine ring; ring X is a heterocyclic ring as defined in the specification; A is phenylene or 5-7C cycloalkylene, or a 1-8C alkylene into which is optionally inserted one or two groups; D is O or S; and $R^3$ and $R^4$ are hydrogen or a variety of radicals described in the specification: and the pharmaceutically-acceptable acid-addition salts thereof. Manufacturing processes and pharmaceutical compositions are also described.

9 Claims, No Drawings

HALOALKYLGUANIDINE COMPOUNDS, PHARMACEUTICAL COMPOSITIONS AND METHODS, PROCESSES AND INTERMEDIATES

This invention relates to guanidine derivatives which are histamine H-2 antagonists and which inhibit gastric acid secretion.

It is postulated that the physiologically-active compound histamine, which occurs naturally within the animal body, is able to combine, in the course of exerting its activity, with certain specific receptors of which there are at least two distinct and separate types. The first has been named the H-1 receptor (Ash and Schild, *Brit. J. Pharmac.* 1966, 27, 427) and the action of histamine at this receptor is blocked (antagonised) by classical "antihistamine" drugs such as mepyramine. The second histamine receptor has been named the H-2 receptor (Black et al., *Nature*, 1972, 236, 385) and the action of histamine at this receptor is blocked by drugs such as cimetidine. It is known that one of the results of the blockade of the action of histamine at the H-2 receptor is the inhibition of the secretion of gastric acid and a compound which possesses this ability is therefore useful in the treatment of peptic ulcers and other conditions caused or exacerbated by gastric acidity.

In U.K. patent application No. GB2052478A and Japanese patent application No. J56108777 (Derwent Accession No. 74736 D/41) there are described histamine H-2 receptor antagonists which are 2-guanidino-thiazole derivatives carrying a side chain in the 4-position to the end of which is attached a carbamoyl group. It has now been discovered that a haloalkylguanidino-heterocycle carrying a side chain to the end of which is attached an optionally substituted carbamoyl group is a potent histamine H-2 receptor antagonist.

According to the invention there is provided a guanidine derivative of the formula I:

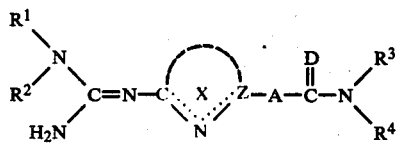
                                   I in which $R^1$ and $R^2$, which may be the same or different, are hydrogen atoms or branched or unbranched 1–10C alkyl, 3–8C cycloalkyl or 4–14C cycloalkylalkyl radicals, each alkyl, cycloalkyl or cycloalkylalkyl radical being optionally substituted by one or more halogen atoms selected from fluorine, chlorine and bromine atoms, provided that at least one of $R^1$ and $R^2$ is a halogen-substituted alkyl, halogen-substituted cycloalkyl or halogen-substituted cycloalkylalkyl radical and provided there is no halogen-substituent on the carbon atom of the alkyl, cycloalkyl or cycloalkylalkyl radical which is directly attached to the nitrogen atom, or $-R^2$ is a hydrogen atom and $-R^1$ is a radical of the formula II:

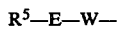
                                     II in which W is an unbranched 2–6C alkylene chain which is optionally substituted by one or two 1–4C alkyl radicals, E is an oxygen or sulphur atom, a sulphinyl or sulphonyl radical, or a radical of the formula $NR^6$ in which $R^6$ is a hydrogen atom or a 1–6C alkyl radical, $R^5$ is a hydrogen atom or an unbranched 1–6C alkyl radical which is optionally substituted by one or two 1–4C alkyl radicals, or $R^5$ and $R^6$ are joined to form, together with the nitrogen atom to which they are attached, a pyrrolidine, piperidine, morpholine, piperazine or N-methylpiperazine ring; in ring X the dotted line is a double bond on one side of the nitrogen atom N and Z is a carbon or nitrogen atom such that ring X is a 5- or 6-membered aromatic heterocyclic ring which contains at least one nitrogen atom and may optionally contain one or two additional hetero atoms selected from oxygen, nitrogen and sulphur atoms, which heterocyclic ring may, where possible, carry one or two optional substituents, the optional substituents on ring X being selected from fluorine, chlorine and bromine atoms and 1–6C alkyl, 1–6C alkoxy, trifluoromethyl, hydroxy and amino radicals;

A is a phenylene or 5–7C cycloalkylene radical or a 1–8C alkylene chain which is optionally substituted by one or two 1–3C alkyl radicals and into which is optionally inserted, as part of the backbone of the chain, one or two groups selected from oxygen and sulphur atoms and NH, 1–6C N-alkyl, cis and trans vinylene, ethynylene, phenylene and 5–7C cycloalkylene radicals, provided that the shortest link between ring X and C=D is of at least 3 atoms, provided that when an optional insertion is made in chain A which results in the inserted group being directly attached to C=D the inserted group is other than an oxygen or sulphur atom or an NH or N-alkyl radical, and provided that no two insertions selected from oxygen and sulphur atoms and NH and N-alkyl radicals are directly attached one to the other;

D is an oxygen or sulphur atom, in particular an oxygen atom;

$R^3$ is a hydrogen atom or a hydroxy, amino, 1–6C alkylamino, 1–6C haloalkylamino, 1–6C alkanoylamino, 1–6C alkyl, 3–8C cycloalkyl, 4–12C cycloalkylalkyl, 2–6C alkenyl, 2–6C alkynyl, 1–6C haloalkyl, (the halo or halos of the 1–6C haloalkylamino and the 1–6C haloalkyl being selected from one or more of the group of fluorine, chlorine, bromine and iodine), 1–6C alkoxy, 1–6C hydroxyalkyl, 2–10C alkoxyalkyl, 2–10C alkylthioalkyl, 1–6C aminoalkyl, 2–8C alkylaminoalkyl, 3–12C dialkylaminoalkyl, 2–8C alkanoylaminoalkyl, 8–14C aroylaminoalkyl, 3–10C alkoxycarbonylalkyl, 2–8C carbamoylalkyl, 6–10C aryl, 7–11C arylalkyl, heteroaryl or heteroarylalkyl radicals, wherein the heteroaryl part is a heterocyclic aromatic ring containing one, two or three hetero atoms selected from oxygen, nitrogen and sulphur atoms, wherein the alkyl part of the heteroarylalkyl radical is 1–6C and wherein, when $R^3$ is or contains an aryl or heteroaryl ring, that ring is optionally substituted by one or two groups selected from fluorine, chlorine, bromine and iodine atoms and 1–6C alkyl, 1–6C alkoxy, 1–6C alkylthio, 2–6C dialkylamino, 2–6C alkanoyl, trifluoromethyl, hydroxy and amino radicals; $R^4$ is a hydrogen atom or $R^3$ is alkyl and $R^3$ and $R^4$ are joined to form, together with the nitrogen atom to which they are attached, a 5-, 6- or 7-membered saturated ring which optionally contains a double bond or an additional oxygen atom, NH or 1–6C N-alkyl radical; and the pharmaceutically-acceptable acid-addition salts thereof.

It is to be understood that, in the above formula I and throughout this specification, although the double bond in the guanidine residue attached to ring X has been inserted in a particular position, other tautomeric forms are possible, and this invention includes such tautomeric forms within its scope, both in terms of the compounds of the invention and in terms of the manufacturing processes. It is also to be understood that when A is or contains a cycloalkylene radical the groups attached to this radical may be in the cis or trans configuration. When A is or contains a cycloalkylene radical and/or when A is an alkylene chain substituted by one or two alkyl radicals the compound of the formula I will, in most instances, contain at least one asymmetric centre. In such cases the compound of the formula I will therefore exist in at least two enantiomeric forms, the precise number being determined by the number of asymmetric centres. The biological activity, as hereinafter defined, of these enantiomeric forms may differ, and it is therefore to be understood that this invention encompasses the racemate of the formula I, including any possible diastereoisomeric forms, and any enantiomeric form which possesses the disclosed biological activity, it being a matter of common general knowledge to one skilled in the art how to separate diastereoisomeric forms and how to separate a racemate into its enantiomers and determine the biological activity of each.

A particular value for $R^1$ or $R^2$ when it is a halogen-substituted alkyl radical is a 2,2,2-trifluoroethyl, 2,2,2-trichloroethyl, 2-chloro-2,2-difluoroethyl, 2,2-dichloro-2-fluoroethyl, 2-bromo-2,2-difluoroethyl, 2,2-dibromo-2-fluoroethyl, 2-fluoroethyl, 2-chloroethyl, 2,2-difluoroethyl, 2,2-dichloroethyl, 2-chloro-2-fluoroethyl, 2-bromo-2-fluoroethyl, 2,2,3,3-tetrafluoropropyl, 2,2,3,3,3-pentafluoropropyl, 1,1,1,3,3,3-hexafluoroisopropyl, 1,3-dichloro-1,1,3,3-tetrafluoroisopropyl, 1-chloro-1,1,3,3,3-pentafluoroisopropyl, 1,3-difluoroisopropyl or 2,2,3,3,4,4,4-heptafluorobutyl radical.

A particular value for $R^1$ or $R^2$ when it is a halogen-substituted cycloalkyl radical is a 2,2,3,3-tetrafluorocyclopropyl, 2-chloro-2,3,3-trifluorocyclopropyl, 2,2-difluorocyclopropyl, 2-chloro-3,3-difluorocyclopropyl, 2,2,3,3,4,4-hexafluorocyclobutyl or 2-chloro-2,3,3,4,4-pentafluorocyclobutyl radical.

A particular value for $R^1$ or $R^2$ when it is a halogen-substituted cycloalkylalkyl radical is a (1,2,2,3,3-pentafluorocyclopropyl)methyl, (2-chloro-1,2,3,3-tetrafluorocyclopropyl)methyl, (1,2,2,3,3,4,4-heptafluorocyclobutyl)methyl or (2-chloro-1,2,3,3,4,4-hexafluorocyclobutyl)methyl radical.

A particular value for $R^1$ or $R^2$ when it is an alkyl radical is a methyl, ethyl, n-propyl, isopropyl or butyl radical.

A particular value for $R^1$ or $R^2$ when it is a cycloalkyl radical is a cyclopropyl or cyclobutyl radical.

A particular value for $R^1$ or $R^2$ when it is a cycloalkylalkyl radical is a cyclopropylmethyl or cyclobutylmethyl radical.

A particular value for the optional substituent on W is a methyl radical.

A particular value for $R^5$ is a hydrogen atom or a methyl radical.

A particular value for $R^6$ is a hydrogen atom or a methyl radical.

A particular value for the radical of the formula II is a 2-methoxyethyl, 2-hydroxyethyl, 2-methylthioethyl or 2-dimethylaminoethyl radical.

A particular value for the ring X is an oxazole, thiazole, imidazole, 1,2,4-thiadiazole, 1,2,4-oxadiazole, 1,2,3-triazole, 1,2,4-triazole, pyrazole, pyrazine, pyridine, pyrimidine or 1,3,5-triazine ring, each being optionally substituted, where possible, by one or two substituents selected from fluorine, chlorine and bromine atoms and methyl, methoxy, trifluoromethyl, hydroxy and amino radicals.

A particular value for —A— is a phenylene, cyclopentylene, cyclohexylene, trimethylene, tetramethylene, pentamethylene, thioethylene, thiotrimethylene, thiotetramethylene, thiopentamethylene, oxyethylene, oxytrimethylene, oxytetramethylene, methylenethiomethylene, methylenethioethylene, methylenethiopropylene, methyleneoxymethylene, methyleneoxyethylene, ethyleneoxyethylene, oxy-2-methylethylene, thiopropylenethiomethylene, oxyethyleneoxymethylene, iminoethylene, iminopropylene, vinylenepropylene, oxymethylenevinylene, 1,3-phenylene, 1,3-cyclopentylene, methylene-1,4-phenylene, ethyleneoxymethylene-1,4-phenylene, oxy-1,3-phenylenemethylene or thiomethyleneethynylenemethylene radical. These values for —A— are written reading from left to right in formula I such that the first named part of the radical is attached to ring X and the last named part of the radical is attached to C═D. Thus, for example, when —A— is a thiomethyleneethynylenemethylene radical, the compound of the formula I contains the part structure III:

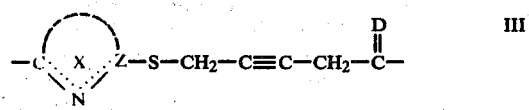

A particular value for $R^3$ is a hydrogen atom or a hydroxy, amino, methylamino, 2,2,2-trifluoroethylamino, acetylamino, methyl, cyclohexyl, cyclohexylmethyl, allyl, propargyl, 2,2,2-trifluoroethyl, methoxy, 2-hydroxyethyl, 2-methoxyethyl, 2-methylthioethyl, 2-aminoethyl, 2-methylaminoethyl, 2-dimethylaminoethyl, 2-acetylaminoethyl, 2-benzoylaminoethyl, methoxycarbonylmethyl, 2-carbamoylpropyl, phenyl, benzyl, heteroaryl and heteroarylmethyl, in the latter two of which the heteroaryl part is a furan, thiophene, pyrrole, thiazole, oxazole, imidazole, thiadiazole, oxadiazole, triazole, pyrazole, pyridine or pyrimidine ring, and wherein when $R^3$ is or contains a phenyl or heteroaryl ring, that ring is optionally substituted by one or two groups selected from fluorine, chlorine, bromine and iodine atoms and methyl, methoxy, methylthio, dimethylamino, acetyl, trifluoromethyl, hydroxy and amino radicals.

A particular value for the ring formed when $R^3$ and $R^4$ are joined is a pyrrolidine, piperidine, morpholine, piperazine or N-methylpiperazine ring.

The following are 7 preferred features of the guanidine derivative of the formula I. When any one of these features is taken, either singly or in combination, with the other general or particular features of the guanidine derivative of the formula I listed above, there are obtained preferred sub groups of compounds within the above general definition.

1. $R^3$ and $R^4$ are hydrogen atoms.
2. $R^2$ is a hydrogen atom and $R^1$ is a 2,2,2-trifluoroethyl, 2-chloro-2,2-difluoroethyl or 2,2,3,3-tetrafluoropropyl radical.
3. Ring X carries no optional substituent.
4. Ring X is a pyrazole, 1,2,3-triazole, 1,2,4-triazole in which A is linked at the 1-position, pyrimidine in which A is linked at the 2-position, or thiazole in which A is linked at the 4-position, ring.

5. Ring X is a pyrazole, 1,2,3-triazole, or 1,2,4-triazole in which A is linked at the 1-position, ring.

6. Ring X is a pyrazole ring.

7. —A— is a tetramethylene, pentamethylene, oxytrimethylene, oxytetramethylene, thiatrimethylene or thiatetramethylene radical.

Specific compounds of the invention are set out in the Examples. The following is a preferred group of compounds.

4-[4-(2-[2,2,2-trifluoroethyl]guanidino)pyrimid-2-ylthio]butyramide (Example 6);

5-[3-(2-[2,2,2-trifluoroethyl]guanidino)pyrazol-1-yl]valeramide (Example 10);

5-[3-(2-[2,2,3,3-tetrafluoropropyl]guanidino)pyrazol-1-yl]valeramide (Example 19);

5-[3-(2-[2-chloro-2,2-difluoroethyl]guanidino)pyrazol-1-yl]valeramide (Example 20), 5-[4-(2-[2,2,2-trifluoroethyl]guanidino)-1,2,3-triazol-2-yl]valeramide (Example 21);

5-[4-(2-[2,2,3,3-tetrafluoropropyl]guanidino)-1,2,3-triazol-2-yl]valeramide (Example 23);

6-[4-(2-[2,2,2-trifluoroethyl]guanidino)-1,2,3-triazol-2-yl]hexanoamide (Example 24);

4-[4-(2-[2,2,3,3-tetrafluoropropyl]guanidino)pyrimid-2-yloxy]butyramide (Example 44);

4-[2-(2-[2,2,3,3-tetrafluoropropyl]guanidino)pyrid-6-ylthio]butyramide (Example 62);

and the pharmaceutically-acceptable acid-addition salts thereof.

Among this group of compounds, the compounds of Examples 10, 19 and 44 are preferred and the compound of Example 10 is particularly preferred.

A suitable pharmaceutically-acceptable acid-addition salt of the guanidine derivative of the formula I is, for example, a salt formed with hydrochloric, hydrobromic, phosphoric, sulphuric, acetic, citric or maleic acid.

The guanidine derivative of the invention may be manufactured by methods in which the actual chemical reactions involved are known in themselves. The following processes, $R^1$, $R^2$, $R^3$, $R^4$, A, D and ring X having the meanings stated above, unless indicated otherwise, are therefore provided as further features of the invention.

The process of the invention is characterised by:

(a) reaction of a compound of the formula IV:

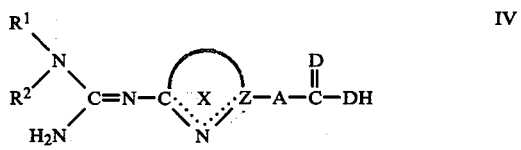

IV or an activated derivative thereof with a compund of the formula $R^3R^4NH$. The activated derivative may, for example be an ester, for example a 1-6C ester, for example a methyl or ethyl ester, or an acid halide, for example an acid chloride or acid bromide. Alternatively the activated derivative may be an anhydride, for example, a mixed anhydride. Particularly useful mixed anhydrides are those formed by reaction of the compound of the formula IV with a chloroformate, for example ethyl chloroformate or isobutyl chloroformate. The reaction may be conducted in a diluent or solvent such as methanol, ethanol, methylene dichloride, tetrahydrofuran or dimethylformamide and the reaction may be accelerated or completed by the application of heat, for example by heating to the boiling point of the diluent or solvent. When the activated derivative is an acid halide it is advantageous to conduct the reaction in the presence of a base such as triethylamine and to use a non-alcoholic diluent or solvent.

(b) for those compounds in which $R^3$ and $R^4$ are hydrogen atoms and D is an oxygen atom, hydrolysis of a compound of the formula V:

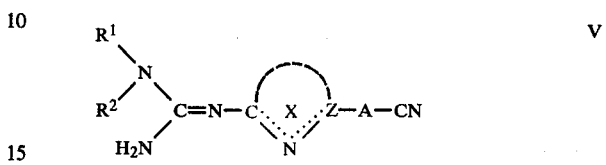

V

The hydrolysis is preferably carried out by use of a strong mineral acid such as concentrated sulphuric acid or by the use of hydrogen peroxide in a basic medium, for example in the presence of sodium hydroxide.

(c) construction of the guanidine radical attached to ring X by reaction of the appropriate thiourea, or a 1-6C S-alkyl (e.g. S-methyl) or S-benzyl derivative thereof, or a salt of such a derivative, with the appropriate amine. The guanidine radical in the compound of the formula I contains three nitrogen atoms each of which carries different substituents. The appropriate amine for use in this reaction may therefore be ammonia, an amine of the formula $R^1R^2NH$ or an amine of the formula VI:

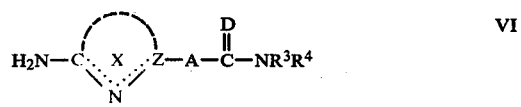

VI

The reaction may be conducted using an excess of one of the reactants as a diluent or solvent, or an additional diluent or solvent, for example methanol or ethanol, may be added. In many cases it is advantageous to use a catalyst such as mercuric oxide, lead oxide or sodium hypochlorite. The reaction may be conducted at ambient temperature or it may be accelerated or completed by the application of heat, for example by heating to the boiling point of the diluent or solvent.

(d) construction of the guanidine radical attached to ring X by reaction of the appropriate cyanamide with the appropriate amine. Since the guanidine radical in the compound of the formula I contains only one unsubstituted nitrogen atom there are two appropriate amines, namely the amine of the formula $R^1R^2NH$ or of the formula VI given above.

(e) for those compounds in which the group inserted into A is an oxygen or sulphur atom or an NH or N-alkyl radical, reaction of a compound of the formula VII or VIII:

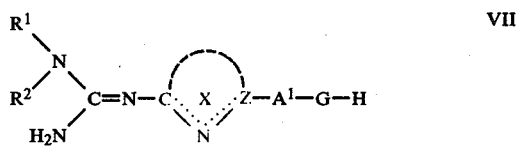

VII

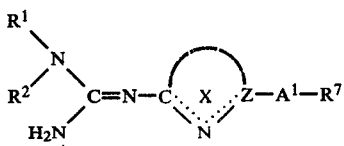

with a compound of the formula IX or X respectively:

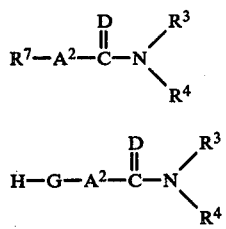

in which G is an oxygen or sulphur atom or an NH or N-alkyl radical, $R^7$ is a displaceable radical and $A^1$ and $A^2$ are fragments of A, including direct bonds, and are such that $A^1$—G—$A^2$ falls within the definition of A given above. $R^7$ is, for example, a halogen atom, for example a chlorine, bromine or iodine atom. When $R^7$ is directly attached to ring X $R^7$ may, for example, be a methylsulphinyl or methylsulphonyl radical.

(f) for those compounds in which Z is a nitrogen atom, reaction of a compound of the formula XI:

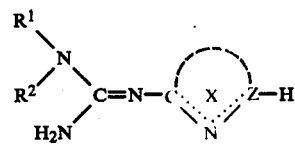

with a compound of the formula XII:

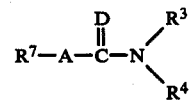

in which $R^7$ is a displaceable radical. $R^7$ is, for example, a halogen atom, for example a chlorine, bromine or iodine atom.

(g) for those compounds in which ring X is a thiazole ring, reaction of a compound of the formula XIII:

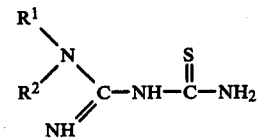

with a compound of the formula XIV:

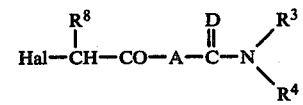

in which Hal is a chlorine or bromine atom and $R^8$ is a hydrogen atom or the optional substituent on the thiazole ring. The reaction may be conducted in a diluent or solvent such as acetone and may be accelerated or completed by the application of heat, for example by heating to the boiling point of the diluent or solvent.

When the process of the invention manufactures the compound of the formula I in the form of the free base and an acid-addition salt is required, the compound of the formula I in the free base form is reacted with an acid which affords a pharmaceutically-acceptable anion.

The starting material of the formula IV for use in process (a) may be obtained by separate construction of the two side chains on the appropriate ring X. Thus the left-hand side chain may be constructed by reduction of a nitro group to an amino group, reaction of this amino group with an isothiocyanate of the formula $R^1R^2N$=C=S, and finally reaction of the resulting thiourea with ammonia in the presence of mercuric oxide. The method of construction of the right hand side chain may vary depending on the nature of ring X, the nature of the atom in ring X to which A is attached (carbon or nitrogen) and the presence or absence of inserted atoms or groups in chain A. In this construction it may be necessary to protect the acid function as a cyano or ester group and to hydrolyse to the acid as a final step. When A contains no inserted group or the inserted group is a phenylene radical and Z is a carbon atom, it is preferable to construct the ring X with the right hand chain already in place. Thus when ring X is a thiazole ring a process similar to that described in process (g) may be used, for example as illustrated in Examples 51, 52, 53 and 54. When ring X is a 1,2,3-triazole ring, it may be formed by reaction of methazonic acid with a suitable azide, for example as illustrated in Example 26. When ring X is a pyrimidine, it may be formed by reaction of a suitably substituted imino ether with 2-chloroacrylonitrile, for example as illustrated in Example 31. When the inserted group in A is vinylene or ethynylene radical, A may be introduced by formation of the double or triple bond by standard coupling methods, for example as illustrated in Example 48. When the inserted group in A is a cycloalkylene radical, the chain A may be constructed by a conjugate addition to the corresponding cycloalk-2-enone, for example as illustrated in Example 25. When the inserted group in A is an oxygen or sulphur atom or an NH or N-alkyl radical, the right hand chain may be built up by a method similar to that described in process (e), for example as illustrated in Examples 1, 6, 29, 41, 47, 49, 56, 57, 59, 60, 61 and 62. When Z is a nitrogen atom, the right hand chain may be formed by a method similar to that described in process (f), for example as illustrated in Examples 11, 21, 55 and 58.

The starting material of the formula V for use in process (b) may be prepared by methods exactly analogous to the methods of preparation of the compound of the formula IV. Indeed, as already explained, the compound of the formula V may be an immediate precursor of the compound of the formula IV.

The starting material of the formula VI for use in process (c) may be prepared by the methods described above for the preparation of the compounds of the formula IV or V in which the right hand chain is constructed first, followed by use of one of the processes (a) or (b).

The cyanamide, corresponding to the amine of the formula VI, for use in process (d) may be prepared by reaction of the compound of the formula VI with cyanogen bromide.

The starting materials of the formulae VII and VIII for use in process (e), and of the formula XI for use in process (f), may be prepared by construction of the guanidine chain on a suitably substituted ring X.

The starting material of the formula IV for use in process (a) is a particularly useful intermediate for preparing the compounds of the formula I. This starting material, and the activated derivatives (1–6C alkyl ester, acid chloride, acid bromide, mixed anhydride) thereof and therefore provided as a further feature of this invention. Particularly useful mixed anhydrides are those formed with 1–6C alkyl chloroformates, for example ethyl and isobutyl chloroformates.

The starting material of the formula V for use in process (b) is a particularly useful intermediate for preparing the compounds of the formula I. This starting material is therefore provided as a further feature of the invention.

As noted above, the guanidine derivative of the invention is a histamine H-2 antagonist, inhibits the secretion of gastric acid in warm-blooded animals and is therefore useful in the treatment of peptic ulcers and other conditions caused or exacerbated by gastric acidity, including stress ulcers and gastrointestinal bleeding due to trauma.

The histamine H-2 antagonist activity may be demonstrated on standard tests, for example by the ability of the compound of the formula I to inhibit the histamine-induced positive chronotropic response in the spontaneously beating right atrium of the guinea pig or by its ability to inhibit the histamine-induced uptake of aminopyrine into the acid space of parietal cells.

The guinea pig atrium test is carried out as follows:

A guinea pig right atrium is suspended at 1 g. tension (isometric) in a thermostatically-controlled (30° C.) tissue bath (25 ml.) containing oxygenated (95% $O_2$, 5% $CO_2$) Krebs-Henseleit buffer (pH 7.4). The tissue is allowed to stabilise over 1 hour during which time it is washed 2–4 times. Individual contractions are recorded with a force-displacement transducer through a strain gauge coupler, and instantaneous rates are monitored with a cardiotachometer. A control response to 1 $\mu$M histamine is obtained after which the tissue is washed 3 times and allowed to re-equilibrate to basal rate. After re-equilibration for 15 minutes, the test compound is added to the desired final concentration. Ten minutes after addition of the compound histamine (1 $\mu$M) is again added and the response to histamine in the presence of antagonist is compared to the histamine control response. The result is expressed as a percentage of the histamine control response. Thereafter the apparent dissociation constant of the H-2 antagonist is determined by standard procedures.

The aminopyrine test is carried out as follows:

Gastric mucosa from the New Zealand white rabbit is removed from the underlying muscle and washed in Buffer 1 [containing per liter NaCl; (8.007 g.), KCl (0.201 g.), $Na_2HPO_4$ (0.113 g.), $KH_2PO_4$ (0.204 g.), $CaCl_2.2H_2O$ (0.132 g.), $MgCl_2$ (0.101 g.) and glucose (1 g.), adjusted to pH 7.4 with NaOH]. The tissue is finely chopped, suspended in Buffer 1 and washed three times with Buffer 1. The tissue is then suspended in dispersion medium [collagenase (Sigma Chemical Co., Type V; 100 mg.) and bovine serum albumin (Miles Laboratories Ltd., Fraction V; 100 mg.) in Buffer 1 (100 ml.); 50 ml. per 10 g. net weight of tissue] and incubated at 30° C. and pH 7.4 (maintained by continuous monitoring) with stirring under an oxygen atmosphere. After 30 minutes the tissue is allowed to settle and the supernatant liquid is removed. Fresh dispersion medium (50 ml. per 10 g. wet weight of tissue) is added and incubation is continued with the tissue being largely dispersed into glands and whole cells after 40–60 minutes. Any remaining large pieces of tissue are removed by filtration through nylon mesh. The mixture of glands and cells is collected by centrifugation at 200×g and suspended in Buffer 1 containing 1% bovine serum albumin (Miles Laboratories Ltd., Fraction V). Finally the cells and glands are washed 3 times with Buffer 1 and suspended in Buffer 2 [containing Eagles MEM (500 ml.), Aprotinin (Sigma Chemical Co., 10 mg.) and HEPES (2-[4-(2-hydroxyethyl)piperazin-1-yl]ethanesulphonic acid; 150 mM., 20 ml.) adjusted to pH 7.4 with NaOH; 150 ml. per 10 g. net weight of tissue]. The tissue suspension is stirred under an oxygen atmosphere at 32° C. for at least 1 hour before use. The tissue suspension is incubated with the test compound and aminopyrine (10 $\mu$M) labelled with $C^{14}$ on the dimethylamino group (0.1 $\mu$Ci/ml.) for 20 minutes. The uptake of the aminopyrine is then stimulated by addition of histamine and the phosphodiesterase inhibitor ICI 63197 (*Biochem. Soc. Special Publication* 1, 1973, pp 127–132) to final concentrations of $10^{-5}$ M. and $5 \times 10^{-7}$ M. respectively. After 18 minutes the cells/glands are separated from the incubation medium by filtration of the suspension through glass microfibre filters. The cells/glands are quickly (<10 seconds) washed three times with ice-cold Buffer 1. The $C^{14}$ aminopyrine retained by the tissue is measured on a scintillation counter and the degree of inhibition of uptake by the test compound is calculated by reference to a control sample. The concentration of test compound giving 50% inhibition is then calculated graphically from a series of tests run at different concentrations.

All the compounds exemplified in this specification were tested either on the guinea pig atrium test or on the aminopyrine test. All those tested on the guinea pig atrium test are active at or below a bath concentration of 10 $\mu$M. and the more active compounds show complete inhibition of response at this concentration. All those tested on the aminopyrine test gave a 50% inhibition of uptake of aminopyrine at or below a concentration of 3 $\mu$M.

The inhibition of the secretion of gastric acid may be demonstrated in standard tests, for example by the ability of the compound of the formula I, when dosed intravenously, intragastrically or orally, to inhibit the secretion of acidic gastric juice in, for example, rats, or dogs provided with gastric fistulae or denervated fundic pouches, and whose gastric secretion is stimulated by administration of a secretagogue, for example histamine, pentagastrin, bethanechol or food.

The test in rats is carried out as follows:

Female rats (200–230 g.) are anesthetized by intramuscular administration of urethane (1.5 g/kg.) and the trachea cannulated. A soft tube is passed down the oesophagus into the stomach and secured by a tie in the neck region. A multi-orifice plastic tube (3 mm. diameter) is passed into the antral region of the stomach, via an incision in the duodenum, and tied in place by means of a ligature around the pylorus. Saline (9 g./l. NaCl) is perfused through the stomach via the oesophageal cannula at a rate of 7 ml./minute and collected into beakers from the pyloric outlet over periods of 10 minutes. Acid secretion is stimulated by subcutaneous administration of the specific H-2 agonist dimaprit in a loading dose of 10 mg./kg. followed by an infusion of 30 mg./kg./hour. Acid output is computed by titration of the 10 minute samples to an end point of pH 6.4 with 20 mM. NaOH. When secretion has reached a plateau (three consecutive readings within 5%) the test compound is administered intravenously via a cannula placed in the left external jugular vein. Secretion is then measured for a further 2 hours. A stock solution of each test compound is prepared (10 mg./ml. in DMSO) and appropriate dilution made with saline to enable injection in a dose volume of 1 ml./kg. (DMSO<2%).

The test in dogs provided with chronic fistulae is carried out as follows:

A female pure bred beagle (9–12 kg.) having a chronic gastric fistula is fasted overnight with water ad lib. During the experiment the dog is lightly restrained in a standing position. When studying the test compound by the intravenous route, the fistula is opened and, after ascertaining the absence of basal secretion over a period of 30 minutes, a continuous intravenous infusion of secretagogue (0.5 $\mu$mol./kg./hour of histamine or 2 $\mu$g./kg./hour pentagastrin) in saline (15 ml./hour) is begun. Gastric acid samples are collected every 15 minutes. The volume of each sample is measured and a 1 ml. aliquot is titrated to neutrality with 100 mM NaOH to determine acid concentration. When a plateau of secretion is reached (1–2 hours), the test compound is administered intravenously in saline and gastric acid samples are collected for a further 2–3 hours during which time the infusion of the secretagogue continues uninterrupted.

When studying the test compound by the intragastric route, the absence of basal secretion over a period of 30 minutes is ascertained and the test compound, contained in 25 ml. of 0.5% w/v hydroxypropyl methylcellulose and 0.1% w/v 'Tween' 80 in water ('Tween' is a Trade Mark) is instilled into the stomach through a fistula dosing plug. One hour later, the fistula is reopened and intravenous infusion of a secretagogue, as described above, is immediately begun. Gastric acid samples are measured as described above and the approach of acid secretion to a plateau is compared to that of a control animal which is dosed intragastrically only with the dosing vehicle.

When studying the test compound by the oral route it is administered in a gelatin capsule with 15 ml. of water. One hour later, the fistula is opened and intravenous infusion of the secretagogue is immediately begun. Gastric acid samples are measured as above and the approach of acid secretion to a plateau is compared to that of an undosed control animal.

The test in dogs provided with denervated fundic pouches is carried out as follows:

Male beagle dogs (14–22 kg.) are prepared with vagally denervated pouches of the fundic gland area by the method of Rudick et al. (J. Surg. Res. 1967, 7 383.) The animals are allowed 4–6 weeks to recover from surgery and a further period of 2–3 months prior to routine use, to allow for table training and standardization of secretory responses. The dogs are starved for 23 hours before use (water ad lib) and during experiments they are lightly restrained in cloth slings. After rinsing the pouch with warm water, histamine is infused subcutaneously at a rate of 10 $\mu$g./minute. This dose of agonist produces a submaximal (60–90% of maximum) increase in acid output in all dogs used. Pouch secretions are collected over 15 minute periods into graduated glass test-tubes and the volume measured to the nearest 0.1 ml. A 500 $\mu$l sample is diluted with 5 ml. of saline and titrated to pH 7.0 with 100 mM. NaOH. Total acid output is computed from the product of acid concentration and volume of juice secreted. Compounds are administered intravenously (0.1 ml./kg.) via a cephalic vein or orally in a gelatin capsule when a secretory plateau (3 consecutive readings within 10%) has been attained. Secretion is measured for a period of 3 hours following administration of test compound.

The results obtained in the atrium and aminopyrine tests are predictive of activity in the rat and dog tests.

No overt toxicity or side effects were noted during the rat or dog tests. The compounds 5-(4-[2-(2,2,2-trifluoroethyl)guanidino]pyrimid-2-yl)valeramide, 5-(4-[2-(2,2,2-trifluoroethyl)guanidino]-1,2,3-triazol-2-yl)valeramide, 5-(6-[2-(2,2,3,3-tetrafluoropropyl)guanidino]pyrid-2-yl)valeramide and 5-(3-[2-(2,2,2-trifluoroethyl)-guanidino]pyrazol-1-yl)valeramide were administered intravenously to groups of two anaesthetised rats and four conscious mice at doses which were respectively ten times and one hundred times the dose, in mg./kg., which produced an approximate 50% inhibition of gastric secretion in the anaesthetised rat. No toxic symptoms were noted in any of the dosed animals.

A number of compounds exemplified in this specification exhibit inhibition of acid secretion which shows little or no decline from peak inhibition for several hours.

The N-methylcyanoguanidine group in known H-2 receptor antagonists is potentially changeable into the carcinogenic N-nitroso N-methylcyanoguanidine group in the mammalian body (Pool et al., Toxicology, 1979, 15, 69). The corresponding group in the compounds of the present invention, $CONR^3R^4$, is not potentially changeable into carcinogenic nitroso derivatives when $R^3$ and $R^4$ are hydrogen atoms.

According to a further feature of the invention there is provided a pharmaceutical composition which comprises an guanidine derivative of the invention in association with a non-toxic pharmaceutically-acceptable diluent or carrier.

The pharmaceutical composition may, for example, be in a form suitable for oral, rectal, parenteral or topical administration, for which purposes it may be formulated by means known to the art into the form of, for example, tablets, capsules, aqueous or oily solutions or suspension, emulsions, dispersible powders, suppositories, sterile injectable aqueous or oily solutions or suspensions, gels, creams, ointments or lotions.

In addition to the guanidine derivative of the formula I, the pharmaceutical composition of the invention for oral, rectal or parenteral administration may also contain, or be co-administered with, one or more known drugs selected from antacids, for example aluminium hydroxide—magnesium hydroxide mixtures; antipepsin compounds, for example pepstatin; other histamine H-2 antagonists, for example cimetidine or ranitidine; ulcer healing agents, for example carbenoxolone or bismuth salts; anti-inflammatory agents, for example ibuprofen, indomethacin, naproxen or aspirin prostaglandins, for example 16,16-dimethylprostaglandin $E_2$; classical antihistamines (histamine H-1 antagonists), for example mepyramine or diphenhydramine; anticholinergic agents, for example atropine or propantheline bromide; anxiolytic agents, for example diazepam, chlorodiazepoxide or phenobarbital.

The pharmaceutical composition of the invention for topical administration may also contain, in addition to the guanidine derivative, one or more classical anti-histamines (histamine H-1 antagonists), for example mepyramine or diphenhydramine and/or one or more steroidal anti-inflammatory agents, for example fluocinolone or triamcinolone.

A topical formulation may contain 1–10% w/w of the guanidine derivative of the invention. A preferred pharmaceutical composition of the invention is one suitable for oral administration in unit dosage form, for example a tablet or capsule which contains between 5 mg. and 500 mg. of the guanidine derivative, or one suitable for intravenous, subcutaneous or intramuscular injection, for example a sterile injectable containing between 0.1% and 10% w/w of the guanidine derivative.

The pharmaceutical composition of the invention will normally be administered to man for the treatment of peptic ulcers and other conditions caused or exacerbated by gastric acidity in the same general manner as that employed for cimetidine, due allowance being made in terms of dose levels for the potency and duration of action of the guanidine derivative of the present invention relative to cimetidine. Thus each patient will receive an oral dose of between 5 mg. and 500 mg., and preferably between 10 mg. and 100 mg., of guanidine derivative or an intravenous, subcutaneous or intramuscular dose of between 0.5 mg. and 50 mg., and preferably between 2 mg. and 20 mg., of the guanidine derivative, the composition being administered 1 to 4 times, and preferably once, per day. The rectal dose will be approximately the same as the oral dose. The composition may be administered less frequently when it contains an amount of guanidine derivative which is a multiple of the amount which is effective when given 1–4 times per day.

The invention is illustrated, but not limited, by the following Examples. The n.m.r. spectra are quoted in δ relative to tetramethylsilane (δ=0) as internal standard (s=singlet, d=doublet, t=triplet, q=quartet, m=multiplet, br=broad). The temperatures are in degrees Centigrade. The following contractions are used:

| HOAc | = | acetic acid |
| DMF | = | dimethyl formamide |
| ether | = | diethyl ether |
| DMSO | = | dimethylsulphoxide |
| MeOH | = | methanol |
| EtOH | = | ethanol |
| THF | = | tetrahydrofuran |
| EtOAc | = | ethyl acetate |

Attention is drawn to the fact that 3-nitropyrazole (Examples 10, 11 and 58) and 4-nitrotriazole (Example 21) are both explosion hazards. In the Examples and thoughout the specification, the following abbreviations are used: C,H,N,O. etc. (The conventional chemical symbols for the elements unless otherwise designated).

EXAMPLE 1

A mixture of ethyl 4-[4-(2-[2,2,2-trifluoroethyl]-guanidino)pyramid-2-ylthio]butyrate (0.18 g.) and a 33% w/v solution of methylamine in EtOH (5 ml.) was stirred at room temperature for 4 days and then evaporated to dryness. The residue was recrystallised from EtOAc to give N-methyl-4-[4-(2-[2,2,2-trifluoroethyl]-guanidino)pyrimid-2-ylthio]butyramide (0.09 g.), m.p. 153°–155°.

The ester used as starting material in the above process may be prepared as follows:

A mixture of 2-thiocytosine (0.64 g.), ethyl 4-bromobutyrate (1.07 g.) and 1,5-diazabicyclo[5,4,0]undec-5-ene (0.84 g.) was stirred for 4 hours and then evaporated to dryness. The residue was treated with water and the mixture extracted with EtOAc, and the extract dried and evaporated to dryness to give a gum (1.9 g.). The gum was dissolved in acetonitrile (5 ml.) the solution treated with 2,2,2-trifluoroethyl isothiocyanate (1.1 g.) and the mixture heated at 70° for 72 hours with the addition of further portions of isothiocyanate (0.5 g.) at 24 and 48 hours. The mixture was cooled and the solid which crystallised was collected to give ethyl 4-[4-(3-[2,2,2-trifluoroethyl]thioureido)pyrimid-2-ylthio]butyrate, m.p. 104°–106°.

A mixture of ethyl 4-[4-(3-[2,2,2-trifluoroethylthioureido)pyrimid-2-ylthio]butyrate (0.25 g.), DMF (2 ml.), saturated ethanolic ammonia (5 ml.) and yellow mercuric oxide (0.2 g.) was stirred at room temperature for 2 hours and then filtered. The filtrate was evaporated to dryness and the residue recrystallised from EtOAc to give ethyl 4-[4-(2-[2,2,2-trifluoroethyl]-guanidino)pyrimid-2-ylthio]butyrate, m.p. 120°–122°.

EXAMPLE 2

A mixture of ethyl 4-[4-(2-[2,2,2-trifluoroethyl]-guanidino)pyrimid-2-ylthio]butyrate (0.2 g.), ethanolamine (0.5 ml.) and MeOH (5 ml.) was heated under reflux for 48 hours and then evaporated to dryness. Water was added to the residue, and the mixture extracted with EtOAc. The extract was dried and evaporated to dryness and the residue recrystallised from a small volume of EtOAc to give N-(2-hydroxyethyl)-4-[4-(2-[2,2,2-trifluoroethyl]guanidino)pyrimid-2-ylthio]-butyramide (0.12 g.), m.p. 148°–150°.

EXAMPLE 3

A mixture of ethyl 4-[4-(2-[2,2,2-trifluoroethyl]-guanidino)pyrimid-2-ylthio]butyrate (0.2 g.), ethylenediamine (2 ml.) and MeOH (5 ml.) was kept at room temperature for 18 hours and then heated under reflux for 4 hours. The solution was evaporated to dryness, the residue treated with water, and the mixture extracted with EtOAc. The extract was dried and evaporated to dryness. The residue was dissolved in acetone and the solution added to a solution of maleic acid in acetone. The precipitate was collected to give N-(2-aminoethyl)-4-[4-(2-[2,2,2-trifluoroethyl]-guanidino)pyrimid-2-ylthio]butyramide bis hydrogen maleate (0.22 g.), m.p. 144°–148°.

EXAMPLE 4

By a similar process to that in Example 1, using ethyl 5-[4-(2-[2,2,2-trifluoroethyl]guanidino)pyrimid-2 ylthio]valerate (prepared in an analogous manner to the butyrate used in Example 1) there was obtained N-methyl-5-[4-(2-[2,2,2-trifluoroethyl]guanidino)pyrimid-2-ylthio]valeramide, m.p. 148°–150°.

EXAMPLE 5

By a similar process to that described in Example 2 using ethyl 5-[4-(2-[2,2,2-trifluoroethyl]guanidino)-pyrimid-2-ylthio]valerate as starting material there was obtained N-(2-hydroxyethyl)-5-[4-(2-[2,2,2-trifluoroethyl]guanidino)pyrimid-2-ylthio]valeramide hydrogen maleate, m.p. 179°–181°.

EXAMPLE 6

A mixture of 4-[4-(2-[2,2,2-trifluoroethyl]guanidino)-pyrimid-2-ylthio]butyronitrile (0.14 g.) and concentrated $H_2SO_4$ was left at room temperature for 3 hours and then diluted with crushed ice and water. The solution was basified with 10 N aqueous NaOH and the mixture extracted three times with EtOAc. The combined extracts were dried and evaporated to dryness to give 4-[4-(2-[2,2,2-trifluoroethyl]guanidino)pyrimid-2-ylthio]butyramide (0.13 g.) which was characterised as the hydrogen maleate, m.p. 202°–203° on recrystallisation from aqueous EtOH.

The starting material for use in the above process may be prepared as follows:

4-Chlorobutyronitrile (0.23 g.) in EtOH (2 ml.) was added to a solution of 2-thiocytosine (0.25 g.) in 0.5 N aqueous NaOH (5 ml.) and the mixture stirred for 18 hours. A further portion of 4-chlorobutyronitrile (0.23 g.) was added and the mixture stirred a further 24 hours. The solution was concentrated in vacuo to 2 ml. and cooled and the crystalline precipitate collected to give 4-[4-aminopyrimid-2-ylthio]butyronitrile (0.3 g.), m.p. 99°–100°.

A mixture of 4-[4-aminopyrimid-2-ylthio]butyronitrile (0.25 g.), acetonitrile (3 ml.) and 2,2,2-trifluoroethyl isothiocyanate (0.21 g.) was stirred at 70° for 72 hours and then evaporated to dryness. The residue was crystallised from a mixture of ether and petroleum ether (b.p. 60°–80°) to give 4-[4-(3-[2,2,2-trifluoroethyl]thioureido)pyrimid-2-ylthio]butyronitrile (0.37 g.), m.p. 125°–126°.

A mixture of 4-[4-(3-[2,2,2-trifluoroethyl]thioureido)-pyrimid-2-ylthio]butyronitrile (0.32 g.), saturated ethanolic ammonia (20 ml.) and yellow mercuric oxide (0.5 g.) was stirred at room temperature for 20 hours and then filtered and the filtrate evaporated to dryness. The residue was recrystallised from a mixture of acetone and petroleum ether (b.p. 60°–80°) to give 4-[4-(2-[2,2,2-trifluoroethyl]guanidino)pyrimid- b 2-ylthio]butyronitrile (0.29 g.), m.p. 137°.

EXAMPLES 7 AND 8

By a similar process to that described in Example 6 and using the appropriate nitrile (prepared in an analogous manner to the butyronitrile described in Example 6) as starting material, there were obtained 5-[4-(2-[2,2,2-trifluoroethyl]guanidino)pyrimid-2-ylthio]valeramide hydrogen maleate, m.p. 184°–186° and 6-[4-(2-[2,2,2-trifluoroethyl]guanidino)pyrimid-2-ylthio]hexanoamide hydrogen maleate, m.p. 176°–177°.

EXAMPLE 9

A mixture of 4-(4-[2-(2-methoxyethyl)guanidino]-pyrimid-2-ylthio)butyronitrile (0.16 g.) and concentrated sulphuric acid (2 ml.) was stirred at ambient temperature for 5 hours. The reaction mixture was then cooled in an ice-bath and basified by careful dropwise addition of concentrated aqueous ammonia (s.g. 0.880). The resulting white precipitate was collected, washed with water and then cold EtOH. The solid was dissolved in hot EtOH with maleic acid and the solution allowed to cool. There was thus obtained 4-(4-[2-(2-methoxyethyl)guanidino]pyrimid-2-ylthio)butyramide maleate (0.22 g.), m.p. 194°–195°.

The starting material may be obtained as follows:

To a stirred mixture of 4-[4-aminopyrimid-2-ylthio]-butyronitrile (0.60 g.) and tetrahydrofuran (30 ml.) under argon at −78° was added n-butyl lithium (1.6 molar in hexane; 1.9 ml.). The reaction mixture was stirred for 0.5 hours at −78° and then 2-methoxyethylisothiocyanate (0.35 g.) in tetrahydrofuran (5 ml.) was added dropwise. The reaction mixture was allowed to warm to ambient temperature and stirring was continued for a further 64 hours. The reaction was poured into water and extracted (×3) with EtOAc. The combined extracts were evaporated to dryness to give a crude solid which was purified by medium pressure chromatography on silica using $CHCl_3$/MeOH 9.5:0.25 v/v as eluant. The purified product (0.25 g.) was immediately added to a stirred mixture of EtOh saturated with ammonia (10 ml.) and mercuric oxide (0.22 g.) and stirring was continued for 1.5 hours. The reaction mixture was filtered through diatomaceous earth, the filtrate evaporated and the residue purified by medium pressure chromatography on silica using $CHCl_3$/MeOH/aqueous ammonia (s.g. 0.880) 9.5:0.6:0.05 v/v/v as eluant to give 4-(4-[2-(2-methoxyethyl)guanidino]pyrimid-2-ylthio)butyronitrile (0.16 g.) as a semicrystalline solid which was used without further purification.

EXAMPLE 10

5-[3-(2-[2,2,2-Trifluoroethyl]guanidino)pyrazol-1-yl]valeronitrile (13 g.) was added over 10 minutes to concentrated sulphuric acid (65 ml.) with stirring. The resulting solution was kept at 20° for 18 hours then diluted with ice (300 ml.) and basified to pH 9 with 10.8 N sodium hydroxide. The mixture was extracted with EtOAc (3×200 ml.) and the extract was dried (MgSO4) and evaporated in vacuo to an oil which crystallised. The crude material was recrystallised from EtOAc to give 5-[3-(2-[2,2,2-trifluoroethyl]guanidino)pyrazol-1-yl]valeramide, m.p. 130°. The maleic acid salt was prepared in acetone, m.p. 183°–184°.

The starting material may be prepared as follows:

Sodium hydride paste (6.16 g. of 61% w/w suspension in liquid paraffin) was added portionwise over 30 minutes to a solution of 3-nitropyrazole (17.4 g.) in dry DMF (150 ml.) with external ice cooling to maintain the temperature at 20°–30°. The mixture was stirred for 45 minutes and to the almost clear solution was added 5-bromovaleronitrile (25 g.) over 30 minutes, at 25°–30°, and the mixture was stirred for 4 hours. Water (450 ml.) and EtOAc (450 ml.) was added and the upper layer was separated, dried (MgSO4) and evaporated in vacuo to an oil which was a mixture of 5-(3-nitropyrazol-1-yl)valeronitrile and 5-(5-nitropyrazol-1-yl)valeronitrile. The oil was divided into two 15 g. portions which were fractionated on a silica column (3.5 cm diameter × 100 cm long) eluted at 2 atmospheres by EtOAc/60°–80° petroluem ether (3:7 v/v). The 1.5 isomer was eluted first followed by the 1:3 isomer. The 5-(3-nitropyrazol-1-yl)valeronitrile had m.p. 32°–33°.

To a solution of 5-(3-nitropyrazol-1-yl)valeronitrile (9.16 g.) in dry tetrahydrofuran (200 ml.) was added 5% w/w palladium on carbon (1.8 g.). The mixture was stirred at 20° under an atmosphere of hydrogen. 3.2 Liters of hydrogen were absorbed over 4 hours. The catalyst was filtered off and the filtrate was evaporated in vacuo to give 5-(3-aminopyrazol-1-yl)valeronitrile as an oil.

To a solution of 5-(3-aminopyrazol-1-yl)valeronitrile (7.0 g.) in acetonitrile (25 ml.) was added 2,2,2-trifluoroethylisothiocyanate (6.02 g.). After 15 minutes the solvent was evaporated in vacuo to give 5-(3-[3-(2,2,2-trifluoroethyl)thioureido]pyrazol-1-yl)valeronitrile as a white crystalline solid, m.p. 96°-98°.

The above thiourea (12.5 g.) was dissolved in 8 M ammonia in EtOH (120 ml.). Mercuric oxide (12.8 g.) was added and the mixture was stirred at 20° for 30 minutes. The resulting mixture was filtered and the filtrate was evaporated in vacuo to give 5-[3-(2-[2,2,2-trifluoroethyl]guanidino)pyrazol-1-yl]valeronitrile as an oil. A sample of the oil was dissolved in acetone and 5 molecular equivalents of maleic acid was added. Ether was added to the resulting clear solution to produce the crystalline maleate, m.p. 123°-125°.

Alternatively, the 5-[3-(2-[2,2,2-trifluoroethyl]guanidino)pyrazol-1-yl]valeronitrile may be prepared by reaction of 3-aminopyrazole with 2,2,2-trifluoroethylisothiocyanate, reaction of the resulting thiourea with ammonia in the presence of mercuric oxide and finally alkylation of the nitrogen atom in the 1-position of the product, 3-[2-(2,2,2-trifluoroethyl)guanidino]pyrazole, with 5-bromovaleronitrile.

EXAMPLE 11

To a solution of 5-(3-[3-(2,2,2-trifluoroethyl)thioureido]pyrazol-1-yl)valeramide (0.5 g.) in 6 M ammonia in ethyl alcohol (6 ml.) was added mercuric oxide (0.56 g.) over 5 minutes. The mixture was stirred for 1 hour and filtered. The filtrate was evaporated in vacuo to an oil which was dissolved in EtOAc. Addition of petroleum ether (b.p. 60°-80°) gave 5-[3-(2-[2,2,2-trifluoroethyl]guanidino)pyrazol-1-yl]valeramide as a crystalline solid, m.p. 128°-132°.

The starting material may be obtained as follows:

A solution of 5-(3-nitropyrazol-1-yl)valeronitrile (0.2 g.) in concentrated sulphuric acid (1 ml.) was kept at 20° for 19 hours. The mixture was diluted with water (4 ml.), basified to pH 10 with 10.8 N sodium hydroxide and extracted with EtOAc (3×5 ml.). The extracts were dried (MgSO4) and evaporated in vacuo to a white solid which was recrystallised from ethanol to give 5-(3-nitropyrazol-1-yl)valeramide, m.p. 129°-131°.

A mixture of 5-(3-nitropyrazol-1-yl)valeramide (3.6 g.) and 3% w/w palladium on carbon (0.54 g.) was stirred in isopropanol (20 ml.) under an atmosphere of hydrogen. The temperature was kept below 40° by external ice cooling. After 4 hours no more hydrogen was absorbed. The mixture was filtered and the filtrate was evaporated in vacuo to give 5-(3-aminopyrazol-1-yl)valeramide as an oil which crystallised. This product (2.5 g.) was stirred in acetonitrile (25 ml.) and 2,2,2-trifluoroethylisothiocyanate (2.17 g.) was added. After 18 hours the mixture was filtered and the residue was washed with acetonitrile then ether to give 5-(3-[3-(2,2,2-trifluoroethyl)thioureido]pyrazol-1-yl)valeramide, m.p. 172°-174°.

EXAMPLE 12

To a solution of 2,2,2-trifluoroethylcyanamide (0.65 g.) and 5-(3-aminopyrazol-1-yl)valeramide (0.87 g.) in EtOH (10 ml.) was added concentrated hydrochloric acid (5 drops). The resulting mixture was heated under reflux for 5 hours. During this period drops of concentrated hydrochloric acid were added perodically to maintain the pH at 4. Volatile material was evaporated in vacuo and the residue was shaken with 2 N aqueous sodium hydroxide (10 ml.) and EtOAc (35 ml.). The organic layer was separated and the aqueous phase was re-extracted with EtOAc (2×35 ml.). The combined extracts were dried (MgSO4) and maleic acid dissolved in acetone was added to give 5-[3-(2-[2,2,2-trifluoroethyl]guanidino)pyrazol-1-yl]valeramide maleate, m.p. 180°-182°.

The 2,2,2-trifluoroethylcyanamide used as starting material may be obtained as follows:

Cyanogen bromide (1.06 g.) was dissolved in cold ether (5 ml.) and added to a solution of 2,2,2-trifluoroethylamine (1.98 g.) in cold ether (5 ml.). The mixture was allowed to warm to 20° over 30 minutes then filtered. The residue was washed with ether and the combined filtrates were evaporated in vacuo at 20° to give 2,2,2-trifluoroethylcyanamide as a mobile oil which solidified on storage at −15°. The i.r. spectrum showed a band at 2280 cm$^{-1}$ (—CN). The n.m.r. spectrum in d4 methanol with tetramethylsilane as an internal standard (δ=0) had the following resonance: (δ) 3.65 (quartet).

EXAMPLE 13

The process of Example 1 was repeated, using hydrazine in place of methylamine, to obtain 4-[4-(2-[2,2,2-trifluoroethyl]guanidino)pyrimid-2-ylthio]butyric acid hydrazide, m.p. 192°-195°.

EXAMPLES 14–16

The process described in Example 29 was repeated, using 4-[4-(2-[2,2,2-trifluoroethyl]guanidino)pyrimid-2-ylthio]butyric acid and the appropriate amines as starting materials. The following compounds were thus obtained:

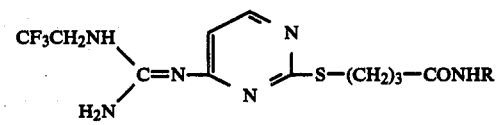

| Example | —R |
|---|---|
| 14 | CF$_3$CH$_2$— |
| 15 | —CH$_2$-(pyridyl) |
| 16 | —OCH$_3$ |

Notes

Example 14: maleate, m.p. 202°-204° (yield 50%).
Example 15: m.p. 176°-178° (yield 47%).
Example 16: maleate, m. p. 161°-163° (yield 15%).
The starting material may be prepared as follows:
A mixture of ethyl 4-[4-(2-[2,2,2-trifluoroethyl]guanidino)pyramid-2-ylthio]butyrate (1.03 g.) and a solution of sodium hydroxide (0.13 g.) in water (10 ml.) was heated under reflux for 1 hour and then cooled. The solution was acidified with glacial HOAc and the white solid which crystallised was collected to give 4-[4-(2-[2,2,2-trifluoroethyl]guanidino)pyrim id-2-ylthio]butyric acid (0.75 g.), m.p. 234°-236°.

EXAMPLES 17–20

The process of Example 10 was repeated, using the appropriate starting materials, to obtain the following compounds.

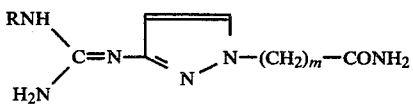

| Example | R— | m |
|---|---|---|
| 17 | CF$_3$CH$_2$— | 3 |
| 18 | CF$_3$CH$_2$— | 5 |
| 19 | CHF$_2$CF$_2$CH$_2$— | 4 |
| 20 | CClF$_2$CH$_2$— | 4 |

Notes

Example 17: 1.25 maleate, m.p. 158°–159° (yield 36%).
Example 18: 1.5 maleate, m.p. 130°–131° (yield 41%).
Example 19: 2 maleate 0.5 H$_2$O, m.p. 93°–95° (yield 58%).
Example 20: 1.25 maleate, m.p. 162°–163° (yield 86%).

The starting materials may be prepared by repeating the second, third, fourth and fifth parts of Example 10 using, where appropriate, 4-bromobutyronitrile or 6-bromohexanonitrile in place of 5-bromovaleronitrile and using, where appropriate, 2,2,3,3-tetrafluoropropylisothiocyanate or 2-chloro-2,2-difluoroethylisothiocyanate in place of 2,2,2-trifluoroethylisothiocyanate.

EXAMPLE 21

A solution of 5-[(4-(2-[2,2,2-trifluoroethyl]-guanidino)-1,2,3-triazol-2-yl]valeronitrile (0.35 g.) in concentrated sulphuric acid (1.0 ml.) was kept at room temperature for 5 hours. The mixture was poured into ice water (5 ml.), basified with aqueous NaOH, saturated with NaCl and extracted with EtOAc. The extract was dried (MgSO$_4$) and evaporated to give a yellow gum. This gum was dissolved in a small volume of EtOAc and treated with a solution of maleic acid (0.14 g.) in a small volume of acetone to give a solution from which the product crystallised. The product was filtered to give 0.33 g. of 5-[4-(2-[2,2,2-trifluoroethylguanidino)-1,2,3-triazol-2-yl]valeramide maleate, m.p. 156°–157°.

The starting material may be obtained as follows:

A stirred solution of 4-nitro-1,2,3-triazole (23.0 g.) in dry DMF (135 ml.) was treated at room temperature with a dispersion of sodium hydride (4.8 g.) in mineral oil (4.8 g.). The mixture was stirred for 30 minutes and then treated with 5-bromovaleronitrile (33.0 g.). The mixture was stirred overnight at room temperature and then poured into water. The product was extracted into EtOAc and purified by column chromatography on silica gel (1 kg.) eluted with EtOAc/petroleum ether (b.p. 60°–80°) (1:1 v/v) to give 22.3 g. of 5-(4-nitro-1,2,3-triazol)-2-yl)valeronitrile as an oil.

A suspension of palladium on charcoal (5% w/w; 0.5 g.) in a solution of 5-(4-nitro-1,2,3-triazol-2-yl)valeronitrile (1.0 g.) in acetic acid (20 ml.) was stirred under one atmosphere of hydrogen until 420 ml. of hydrogen had been absorbed. The mixture was filtered and evaporated to give 0.85 g. of 5-(4-amino-1,2,3-triazol-2-yl)valeronitrile as an oil.

A solution of 5-(4-amino-1,2,3-triazol-2-yl)valeronitrile (0.35 g.) and 2,2,2-trifluoroethylisothiocyanate (0.5 g.) in acetonitrile (5 ml.) was stirred at room temperature overnight. The mixture was evaporated and the residue recrystallised from toluene/petroleum ether (b.p. 60°–80°) to give 0.5 g. of 5-[4-(3-[2,2,2-trifluoroethyl]thioureido)-1,2,3-triazol-2-yl]valeronitrile, m.p. 86°–88° after recrystallisation from toluene.

A stirred solution of 5-[4-(3-[2,2,2-trifluoroethyl]thioureido)-1,2,3-triazol-2-yl]valeronitrile (0.45 g.) in ammoniacal EtOH (6 M; 10 ml.) was treated at room temperature with mercuric oxide (0.6 g.). The mixture was stirred at room temperature for 2 hours. The mixture was filtered and evaporated to give 0.41 g. of 5-[4-(2-[2,2,2-trifluoroethyl]guanidino)-1,2,3-triazol-2-yl)valeronitrile.

EXAMPLES 22–24

The process of Example 21 was repeated, using the appropriate starting materials, to obtain the following compounds.

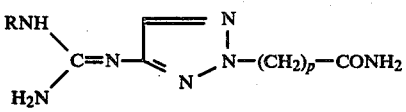

| Example | R— | p |
|---|---|---|
| 22 | CF$_3$CH$_2$— | 3 |
| 23 | CHF$_2$CF$_2$CH$_2$— | 4 |
| 24 | CF$_3$CH$_2$— | 5 |

Notes

Example 22: maleate, m.p. 159°–161° (yield 53%).
Example 23: maleate, m.p. 141°–142° (yield 58%).
Example 24: maleate, m.p. 146°–147° (yield 49%).

The starting materials may be prepared by repeating the second, third, fourth and fifth parts of Example 21 using, where appropriate, 4-bromobutyronitrile or 6-bromohexanonitrile in place of 5-bromovaleronitrile, and using, where appropriate, 2,2,3,3-tetrafluoropropylisothiocyanate in place of 2,2,2-trifluoroethylisothiocyanate.

EXAMPLE 25

A mixture of 3-[4-(3-[2,2,2-trifluoroethyl]thioureido)-1,2,3-triazol-2-yl]cyclopentanecarboxamide (0.34 g.), mercuric oxide (0.4 g.) and methanolic ammonia (6 M; 20 ml.) was stirred at room temperature for 3 hours. The mixture was kept at room temperature overnight, filtered, and evaporated to give 0.27 g. of 3-[4-(2-[2,2,2-trifluoroethyl]guanidino)-1,2,3-triazol-2-yl]cyclopentanecarboxamide. A sample in a small volume of EtOAc was treated with an equivalent of maleic acid in a small volume of acetone to give, on addition of ether, 3-[4-(2-[2,2,2-trifluoroethyl]guanidino)-1,2,3-triazol-2-yl]cyclopentanecarboxamide maleate, m.p. 143°–146°.

The starting material may be prepared as follows:

A mixture of 1,2,3-triazole (3.5 g.), cyclopent-2-enone (5.0 g.), benzyltrimethylammonium hydroxide (40% w/v solution in MeOH; 2.0 ml.) and dioxan (20 ml.) was stirred at room temperature overnight. The mixture was evaporated, treated with EtOAc, washed twice with water and once with brine, dried (MgSO$_4$), and evaporated to give unpurified 3-(1,2,3-triazol-2-yl)cyclopentanone as a pale yellow oil. The n.m.r. spectrum of the product exhibited the following resonances: 7.62 (s, 2H); 5.37 (br quintet, 1H); 3.1–1.8 (m, 6H). (solvent CDCl$_3$)

A mixture of unpurified 3-(1,2,3-triazol-2-yl)cyclopentanone (0.5 g.), lithium aluminium hydride (0.5 g.) and ether (20 ml.) was stirred at room temperature overnight. The excess of lithium aluminium hydride was destroyed with aqueous NaOH. The reaction mixture was filtered and evaporated to give 0.5 g. of unpurified 3-(1,2,3-triazol-2-yl)cyclopentanol as an oil.

A solution of unpurified 3-(1,2,3-triazol-2-yl)cyclopentanol (0.44 g.) in pyridine (5 ml.) was treated at 5° with toluene-p-sulphonyl chloride (1.1 g.). The mixture was kept at 5° overnight and then poured into water and extracted with EtOAc. The extract was washed with water, aqueous HCl (2 N) and brine, and then dried (MgSO4), and evaporated to give 0.72 g. of unpurified 3-(1,2,3-triazol-2-yl)cyclopentyl toluene-p-sulphonate as an oil.

A mixture of unpurified 3-(1,2,3-triazol-2-yl)cyclopentyl toluene-p-sulphonate (0.7 g.), NaCN (0.17 g.) and DMSO (10 ml.) was stirred at 95° overnight. The mixture was poured into water and extracted with EtOAc. The extract was washed with brine, dried (MgSO4), and evaporated to give 0.33 g. of unpurified 3-(1,2,3-triazol-2-yl)cyclopentanecarbonitrile as an oil.

A mixture of unpurified 3-(1,2,3-triazol-2-yl)cyclopentanecarbonitrile (0.3 g.), concentrated sulphuric acid (2 ml.), and concentrated nitric acid (1 ml.) was kept at room temperature overnight. The initial reaction was exothermic and required cooling. The mixture was poured into water and extracted with EtOAc. The extract was washed with brine, dried (MgSO4), and evaporated to give 0.26 g. of unpurified 3-(4-nitro-1,2,3-triazol-2-yl)cyclopentanecarboxylic acid.

A mixture of 3-(4-nitro-1,2,3-triazol-2-yl)cyclopentanecarboxylic acid (0.3 g.) and thionyl chloride (2 ml.) was heated at 60° for 30 minutes. The mixture was evaporated under reduced pressure and then twice treated with toluene (10 ml.) and re-evaporated. The nonvolatile residue was treated with ethanolic ammonia (6 M; 10 ml.). The mixture was evaporated to give 0.25 g. of unpurified 3-(4-nitro-1,2,3-triazol-2-yl)cyclopentanecarboxamide. A sample purified by medium pressure liquid chromatography on silica gel using EtOAc as eluant had m.p. 127°–128°.

A mixture of 3-(4-nitro-1,2,3-triazol-2-yl)cyclopentanecarboxamide (0.28 g.), 5% w/w palladium on charcoal (0.3 g.) and EtOH (20 ml.) was treated at 50° with hydrazine hydrate (0.6 ml.). The reaction was kept at 50° for 15 minutes, filtered, and evaporated to give 0.22 g. of unpurified 3-(4-amino-1,2,3-triazol-2-yl)cyclopentanecarboxamide as a white solid.

A mixture of 3-(4-amino-1,2,3-triazol-2-yl)cyclopentanecarboxamide (0.215 g.), 2,2,2-trifluoroethylisothiocyanate (0.5 g.), acetonitrile (5 ml.), and DMF (1 ml.) was stirred at room temperature for 3 hours. The mixture was evaporated, triturated with EtOH and filtered to give 0.35 g. of solid 3-[4-(3-[2,2,2-trifluoroethyl]thioureido)-1,2,3-triazol-2-yl]cyclopentanecarboxamide which was used without further purification.

EXAMPLE 26

A mixture of 3-[4-(2-[2,2,2-trifluoroethyl]guanidino)-1,2,3-triazol-2-yl]benzoic acid (0.2 g.), thionyl chloride (2 ml.) and THF (10 ml.) was warmed for 10 minutes on a steam bath. The mixture was evaporated under reduced pressure, the residue redissolved in THF (10 ml.) and re-evaporated under reduced pressure. This re-evaporation procedure was repeated once more. The residue was dissolved in THF (10 ml.) and poured into aqueous ammonia (s.g. 0.880; 20 ml.) to give a gummy precipitate. The precipitate was extracted into EtOAc. The extract was dried (MgSO4), concentrated to a small volume and treated with a solution of maleic acid (0.071 g.) in a small volume of acetone to give a precipitate of 0.146 g. of 3-[4-(2-[2,2,2-trifluoroethyl]guanidino)-1,2,3-triazol-2-yl]benzamide, m.p. 199°–201°.

The starting material may be prepared as follows:

Nitromethane (61 g.) was added to a warm (45°14 50°) solution of NaOH (61 g.) in water (122 ml.) at such a rate that the temperature was maintained. At the end of the addition the temperature was raised to 55° for 10 minutes and then allowed to fall back to 50°. The mixture was chilled and neutralised to pH 7 with concentrated hydrochloric acid at ≧10°. The precipitated product was redissolved by the addition of aqueous NaOH (12.5 N; 40 ml.) to give a solution of the sodium salt of methazonic acid.

A solution of NaNO2 (36.2 g.) in water (300 ml.) was added during approximately 30 minutes to a suspension of 3-aminobenzoic acid (68.6 g.) in concentrated hydrochloric acid (126.3 ml.) and water (200 ml.) at 0°–5°. The mixture was filtered to give a solution of 3-carboxybenzenediazonium chloride.

The solution of the sodium salt of methazonic acid was treated at 10° with a cold (5°) solution of 3-carboxybenzenediazonium chloride. A precipitate formed immediately and was dissolved in aqueous NaOH (33% w/w; 100 ml.) to give a dark red solution. The dark red solution was stirred and treated at 25° with acetic anhydride (100 ml.). During this treatment, aqueous NaOH (33% w/w, 200 ml.) was added to keep the mixture basic. The reaction mixture was acidifed with concentrated hydrochloric acid and the precipitated product was isolated by filtration to give 101.2 g. of a light brown solid. A mixture of 23.5 g. of this solid, MeOH (150 ml.) and concentrated sulphuric acid (0.5 ml.) was heated under reflux for 3 hours. The reaction mixture was neutralised with aqueous NaOH (1 N), concentrated, and partitioned between CHCl3 and brine. The CHCl3 phase was dried (MgSO4) and evaporated to give 5.9 g. of a red oil that crystallised slowly. The solid was purified by medium pressure liquid chromatography on a silica gel column using EtOAc as eluant to give 5.3 g. of a solid which was recrystallised twice from isopropanol to give 2.7 g. of methyl 3-(4-nitro-1,2,3-triazol-2-yl)benzoate, m.p. 104°–106°.

A mixture of methyl 3-(4-nitro-1,2,3-triazol-2-yl)benzoate (1.0 g.), 5% w/w palladium on charcoal (0.5 g.) and HOAc (100 ml.) was stirred under one atmosphere of hydrogen until 300 ml. of hydrogen had been absorbed. The reaction was filtered and evaporated to give 0.91 g. of methyl 3-(4-amino-1,2,3-triazol-2-yl)benzoate, m.p. 132°–134° after recrystallisation from MeOH.

A warm mixture of methyl 3-(4-amino-1,2,3-triazol-2-yl)benzoate (0.44 g.) and acetonitrile (5 ml.) was treated with 2,2,2-trifluoroethylisothiocyanate (0.34 g.), allowed to cool, and kept at room temperature for 21 hours. The reaction mixture was filtered, washed with ether and petroleum ether (b.p. 60°–80°), and dried to give 0.63 g. of methyl 3-[4-(3-[2,2,2-trifluoroethyl]thioureido)-1,2,3-triazol-2-yl]benzoate, m.p. 187°–188°.

A mixture of methyl 3-[4-(3-[2,2,2-trifluoroethyl]thioureido)-1,2,3-triazol-2-yl]benzoate (0.5 g.), mercuric oxide (0.4 g.) and ammoniacal EtOH (6 M; 10 ml.) was stirred at room temperature for 2 hours. The mixture was treated with mercuric oxide (0.1 g.) and stirred for another 2 hours. The mixture was filtered and evaporated to give 0.47 g. of methyl 3-[4-(2-[2,2,2-trifluoroethyl]guanidino)-1,2,3-triazol-2-yl]benzoate, m.p. 171°-173° after recrystallisation from EtOAc and petroleum ether (b.p. 60°-80°).

A mixture of methyl 3-[4-(2-[2,2,2-trifluoroethyl]guanidino)-1,2,3-triazol-2-yl]benzoate (0.55 g.), EtOH (10 ml.) and aqueous NaOH (1 N; 1.7 ml.) was stirred at room temperature for 18 hours. The mixture was treated with aqueous NaOH (1 N; 0.6 ml.) and kept at room temperature overnight. The mixture was diluted with aqueous NaOH (1 N), washed with EtOAc, acidified to pH 4, and extracted with EtOAc and THF (2:1 v/v). The extract was dried (MgSO$_4$) and evaporated to give 0.27 g. of 3-[4-(2-[2,2,2-trifluoroethyl]guanidino)-1,2,3-triazol-2-yl]benzoic acid which was used without further purification.

EXAMPLE 27

A mixture of methyl 3-[4-(2-[2,2,2-trifluoroethyl]guanidino)-1,2,3-triazol-2-yl]benzoate (0.12 g.), EtOH (3 ml.) and hydrazine hydrate (1 ml.) was kept at room temperature overnight. The reaction mixture was thrice both diluted with EtOH then evaporated to dryness. The residue was recrystallised from MeOH to give 0.03 g. of 3-[4-(2-[2,2,2-trifluoroethyl]guanidino)-1,2,3-triazol-2-yl]benzoic acid hydrazide, m.p. 209°-210°.

EXAMPLE 28

A mixture of methyl 3-[4-(2-[2,2,2-trifluoroethyl]guanidino)-1,2,3-triazol-2-yl]benzoate (0.2 g.) and ethanolamine (5 ml.) was heated at 80° overnight. The mixture was evaporated and the thick oily residue was purified by chromatography on silica gel using EtOAc and isopropanol (6:1 v/v) as eluant. The product was recrystallised from isopropanol to give N-(2-hydroxyethyl)-3-[4-(2-[2,2,2-trifluoroethyl]guanidino)-1,2,3-triazol-2-yl]benzamide, m.p. 171°-173°.

EXAMPLE 29

To a suspension of 4-[6-(2-[2,2,2-trifluoroethyl]guanidino)pyrazin-2-ylthio]butyric acid (0.25 g.) in THF (10 ml) at 0° was added triethylamine (0.082 g.), followed by ethyl chloroformate (0.088 g.) and the mixture was stirred for 30 minutes. A solution of ammonia in THF (5 ml.) was added and the mixture stirred again for 30 minutes, the temperature being allowed to rise to room temperature. The mixture was evaporated in vacuo, aqueous solution bicarbonate (5 ml.) was added and the mixture extracted with EtOAc (2×25 ml.) After drying (MgSO$_4$) the solution was filtered and evaporated in vacuo to give a pale yellow solid. This was purified by medium pressure liquid chromatography on silica eluted with MeOH/CH$_2$Cl$_2$ (1:10 v/v) to give a solid. This was dissolved in EtOAc containing a trace of EtOH and excess of a solution of maleic acid in EtOAc was added. The resulting precipitate was collected by filtration and recrystallised from EtOH to give 4-[6-(2-[2,2,2-trifluoroethyl]guanidino)pyrazin-2-ylthio]butyramide maleate, m.p. 171°-172° (30% yield).

The starting material may be prepared as follows:

To a solution of 2-amino-6-chloropyrazine (6 g.) in acetonitrile (50 ml.) was added 2,2,2-trifluoroethylisothiocyanate (6 ml.) and the mixture heated under reflux on a steam bath for 6 hours. The mixture was allowed to cool, the resulting solid filtered and recrystallised from toluene to give 2-chloro-6-(3-[2,2,2-trifluoroethyl]thioureido)pyrazine.

To a solution of 2-chloro-6-(3-[2,2,2-trifluoroethyl]thioureido)pyrazine (0.7 g.) in alcoholic ammonia (35 ml.) was added yellow mercuric oxide (0.65 g.) and the mixture was stirred at room temperature overnight. The mixture was filtered and the filtrate evaporated in vacuo to give a pale yellow solid. Recrystallisation from toluene/petroleum ether (b.p. 60°-80°) gave 2-chloro-6-(2-[2,2,2-trifluoroethyl]guanidino)pyrazine, m.p. 139°-140°.

To a solution of sodium hydride (50% w/w dispersion in oil; 1.15 g.) was added 4-mercaptobutyric acid (1.44 g.). 2-Chloro-6-(2-[2,2,2-trifluoroethyl]guanidino)pyrazine (1.0 g.) was added and the mixture heated under reflux on a steam bath overnight. Water was added and the mixture washed with ether. The aqueous phase was acidified to pH 4 with hydrochloric acid to precipitate 4-[6-(2-[2,2,2-trifluoroethyl]guanidino)pyrazin-2-ylthio]butyric acid as a colourless solid, which was collected by filtration, washed with water and sucked dry. This material was used without further purification.

EXAMPLE 30

By a similar process to that described in Example 29, using aniline instead of ammonia, there was obtained N-phenyl-4-[6-(2-[2,2,2-trifluoroethyl]guanidino)pyrazin-2-ylthio]butyramide, m.p. 165°-167° (yield 28%).

EXAMPLE 31

Thionyl chloride (1 ml.) was added dropwise to 5-[4-(2-[2,2,2-trifluoroethyl]guanidino)pyrimid-2-yl]valeric acid (0.3 g.) and the mixture heated gently on a steam bath for 5 minutes. Excess thionyl chloride was removed by evaporation in vacuo and the resulting gum was covered with CH$_2$Cl$_2$ (5 ml.). A solution of aniline (0.105 g.) in CH$_2$Cl$_2$ (0.5 ml.) was added, followed by dropwise addition of triethylamine until basic. After stirring at room temperature for 30 minutes, the mixture was poured into water, the organic phase separated and dried (MgSO$_4$). Filtration and evaporation gave an oil which was dissolved in a small volume of EtOH and excess of a solution of maleic acid in EtOAc added. The resulting precipitate was filtered, washed with EtOH and recrystallized from EtOH to give N-phenyl-5-[4-(2-[2,2,2-trifluoroethyl]guanidino)pyramid-2-yl]valeramide maleate. 0.25 H$_2$O, m.p. 169°-171° (yield 21%).

The starting material may be prepared as follows:

Ethyl 5-cyanovalerimidate (75 g.) was stirred for 18 hours in MeOH (200 ml.) containing ammonium chloride (26.4 g.). The mixture was filtered and the filtrate evaporated to dryness. The residue was then heated under reflux in EtOH (250 ml.) containing triethylamine (285 ml.) and 2-chloroacrylonitrile (106 g.). After 2 hours the mixture was cooled, added to water (1 l.) and the pH adjusted to 4 with HOAc. The aqueous mixture was treated with charcoal, filtered and the filtrate extracted with EtOAc (300 ml.). The aqueous layer was separated and the pH adjusted to 9 with aqueous sodium hydroxide. The aqueous mixture was extracted with EtOAc (2×500 ml.). The combined extracts were evaporated to dryness and the residue was recrystallised from acetonitrile to give 16 g. of 5-(4-aminopyrimid-2-yl)valeronitrile.

A mixture of 5-(4-aminopyrimid-2-yl)valeronitrile (30 g.) and 2,2,2-trifluoroethylisothiocyanate (30 g.) in acetonitrile (50 ml.) was heated under reflux for 18 hours. The mixture was evaporated to dryness and the residue dissolved saturated methanolic ammonia. The resulting solution was stirred and mercuric oxide (48 g.) added. After 2 hours the mixture was filtered through diatomaceous earth and the filtrate evaporated to dryness. The residue was triturated with ether and the solid product filtered off to give 39 g. of 5-[4-(2-[2,2,2-trifluoroethyl]-guanidino)pyrimid-2-yl]valeronitrile.

To 5-[4-(2-[2,2,2-trifluoroethyl]guanidino)pyrimid-2-yl]valeronitrile (2 g.) was added concentrated HCl (10 ml.), and the mixture was heated on a steam bath for 1.75 hours. After cooling and evaporation in vacuo, the residue was dissolved in water and brought to pH 5 with aqueous sodium carbonate solution. The resulting precipitate was filtered, washed with water, then EtOH and dried at 70° under vacuum to give 1.9 g. of 5-[4-(2-[2,2,2-trifluoroethyl]guanidino)pyrimid-2-yl]valeric acid which was used without further purification.

EXAMPLES 32-36

The process of Example 31 was repeated, using the appropriate starting materials, to give the following compounds.

| Example | —R |
|---|---|
| 32 | —N(morpholino: —N O ring) |
| 33 | —NH—C$_6$H$_4$—N(CH$_3$)$_2$ |
| 34 | —N(piperazinyl)N—CH$_3$ |
| 35 | —NH—(1H-tetrazol-5-yl) |
| 36 | —NH—C$_6$H$_4$—COCH$_3$ |

Notes
Example 32: maleate, m.p. 165°–166° (yield 66%)
Example 33: maleate, m.p. 194°–196° (yield 25%)
Example 34: 2 maleate, m.p. 162°–163° (yield 45%)
Example 35: 2.5 maleate. 1H$_2$O, m.p. 165°–168°
Example 36: maleate. 0.5H$_2$O, m.p. 187°–189° (yield 10%).

EXAMPLE 37

To a suspension of 5-[4-(2-[2,2,2-trifluoroethyl)-guanidino)pyrimid-2-yl]valeric acid (0.25 g.) in freshly distilled THF (10 ml.) was added triethylamine (0.093 g.) with ice cooling. After stirring 15 minutes, ethyl chloroformate (0.095 g.) was added dropwise and stirred 30 minutes at 0°. Further triethylamine (0.093 g.) was added, followed by 2,2,2-trifluoroethylamine hydrochloride (0.124 g.), and the mixture was stirred at 0° for 30 minutes, then allowed to come to room temperature. After evaporation in vacuo, aqueous sodium carbonate solution was added and the mixture extracted with EtOAc. The extract was dried (MgSO$_4$) filtered and evaporated in vacuo to give an oil which was dissolved in a small volume of EtOAc and excess of a solution of maleic acid in EtOAc added. Addition of ether, with scratching, caused a colourless solid to precipitate. This was collected and recrystallised from EtOAc to give N-(2,2,2-trifluoroethyl)-5-[4-(2-[2,2,2-trifluoroethyl]guanidino)pyrimid-2-yl]valeronitrile maleate. 0.25H$_2$O, m.p. 135°–140°.

EXAMPLE 38

By a similar procedure to that described in Example 37, using 3-aminopyridazine in place of 2,2,2-trifluoroethylamine, there was obtained N-(pyridazin-3-yl)-5-[4-(2-[2,2,2-trifluoroethyl]guanidino)pyrimid-2-yl]valeramide maleate, m.p. 160°–163° (yield 17%).

EXAMPLE 39

A mixture of 5-[4-(2-[2,2,2-trifluoroethyl]guanidino)-pyrimid-2-yl]valeronitrile hydrogen maleate, prepared as described in Example 31, (0.45 g.) and concentrated sulphuric acid (4 ml.) was stirred at room temperature for 4 hours. The mixture was then added to ice (15 g.) and the pH adjusted to 9 with aqueous sodium hydroxide. The mixture was then evaporated to dryness and the solid residue extracted with a mixture of MeOH and chloroform (1:20 v/v, 150 ml.). The extract was filtered and evaporated to dryness. The residue was treated with maleic acid in acetone to give 0.15 g. of 5-[4-(2-[2,2,2-trifluoroethyl]guanidino)pyrimid-2-yl]valeramide hydrogen maleate. 0.5H$_2$O, m.p. 182°–185°.

EXAMPLE 40

By a similar procedure to that described in Example 39, using the appropriate starting material, there was obtained 6-[4-(2-[2,2,2-trifluoroethyl]guanidino)pyrimid-2-yl]hexanoamide, m.p. 179°–181° (yield 32%).

The starting material may be prepared by repeating the second and third parts of Example 31, using ethyl 6-cyanohexanimidate in place of ethyl 5-cyanovalerimidate.

EXAMPLE 41

A solution of 3-[4-(2-[2,2,2-trifluoroethyl]guanidino)-pyrimid-2-ylthio]propanethiol hydrogen maleate (147 mg.) and sodium methoxide (70 mg.) in MeOH was treated with 2-iodoacetamide (123 mg.) and the solution stirred at room temperature for 24 hours and then evaporated to dryness. The residue was partitioned between water and EtOAc, and the EtOAc phase was dried and evaporated to dryness. The residue was purified by preparative tlc on silica gel using EtOAc/MeOH/concentrated aqueous ammonia (s.g. 0.880) 6:1:0.5 v/v/v as developing solvent to give 2-[3-(4-[2-(2,2,2-trifluoroethyl)guanidino]pyrimid-2-ylthio)propylthio]acetamide as a gum (50 mg.) which was crystallised as the hydrogen maleate salt (m.p. 168°–170°) from EtOAc.

The starting material may be obtained as follows:

A mixture of sodium methoxide (81 mg.), MeOH (10 ml.) 1,3-propanedithiol (1 ml.) and 4-[2-(2,2,2-trifluoroethyl)guanidino]-2-methanesulphinylpyrimidine (280 mg.) (European patent publication No. 30092) was stirred at room temperature for 2 hours and then evaporated to dryness. The residue was partitioned between aqueous 2 N HCl and ether, and the aqueous phase was basified with aqueous 10 N NaOH and extracted with EtOAc. The EtOAc extract was dried and evaporated to dryness and the residue crystallised as the hydrogen maleate from acetone to give 3-[4-(2-[2,2,2-trifluoroethyl]guanidino)pyrimid-2-ylthio)propanethiol hydrogen maleate (260 mg.), m.p. 153°–155°.

EXAMPLE 42

A mixture of 5-[4-(2-[2,2,2-trifluoroethyl]guanidino)-pyrimid-2-yloxy]valeronitrile (0.5 g.) and concentrated sulphuric acid (3 ml.) was warmed until solution was obtained, then stirred 2 hours at room temperature. The mixture was poured into water and basified with potassium carbonate. Extraction with EtOAc gave a yellow gum which was converted in acetone to the maleate of 5-[4-(2-[2,2,2-trifluoroethyl]guanidino)pyrimid-2-yloxy]valeramide (0.38 g.), m.p. 192°–193° (54%).

The starting material may be prepared as follows:

4-Cyanobutanol (10 g.) was added to sodium hydride (2.75 g.) in t-butanol (95 ml.) and the solution warmed to 40°. 4-[2-(2,2,2-Trifluoroethyl)guanidino]-2-methylsulphinylpyrimidine (11.24 g.) was added over 10 minutes and the solution kept at 40° for 2 hours then at room temperature for 18 hours. The solvent was removed under vacuum and the residue washed with water, then ether to give 5-[4-(2-[2,2,2-trifluoroethyl]-guanidino)pyrimid-2-yloxy]valeronitrile (8.5 g.), m.p. 134°–136°.

EXAMPLES 43–45

The process of Example 42 was repeated, using the appropriate starting materials, to give the following compounds.

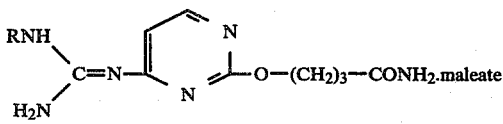

| Example | R— |
|---------|-----|
| 43 | CClF$_2$CH$_2$— |
| 44 | CHF$_2$CF$_2$CH$_2$— |
| 45 | CF$_3$CH$_2$— |

Notes

Example 43: m.p. 149°–153°
Example 44: m.p. 161°–162° (yield 38%)
Example 45: m.p. 189°–191° (yield 69%).

The starting materials for the above process may be prepared by repeating the second part of Example 42 using 3-cyanopropanol in place of 4-cyanobutanol and using, where appropriate, 2-methylsulphinyl-4-[2-(2-chloro-2,2-difluoroethyl)guanidino]pyrimidine or 2-methylsulphinyl-4-[2-(2,2,3,3-tetrafluoropropyl)-guanidino]pyrimidine in place of 2-methylsulphinyl-4-[2-(2,2,2-trifluoroethyl)guanidino]pyrimidine. These two pyrimidine derivatives may be prepared by repeating the second, third and fourth parts of Example 34 in European patent publication No. 30092 using 2-chloro-2,2-difluoroethylisothiocyanate or 2,2,3,3-tetrafluoropropylisothiocyanate respectively in place of 2,2,2-trifluoroethylisothiocyanate.

EXAMPLE 46

A solution of 3-[4-(2-[2,2,2-trifluoroethyl]guanidino)-pyrimid-2-ylmethylthio]propionitrile (850 mg.) in concentrated sulphuric acid (4 ml.) was kept at 20° for 16 hours then added dropwise to saturated aqueous sodium carbonate. The mixture was extracted with EtOAc (3×20 ml.) and the extract dried (MgSO$_4$) and evaporated in vacuo to give 3-[4-(2-[2,2,2-trifluoroethyl]-guanidino)pyrimid-2-ylmethylthio]propionamide as an oil. The maleic acid salt was prepared in acetone (yield 720 mg; 60%), m.p. 168°–169° (decomp.).

The starting material may be prepared as follows:

2-Chloroacrylonitrile (35 ml.) was added in portions over 15 minutes to a solution of chloroacetamidine hydrochloride (55 g.) and triethylamine (120 ml.) in EtOH (250 ml.) cooled to 10°. The temperature was allowed to rise to 40° over 1 hour. The mixture was cooled and filtered and the resulting solution evaporated in vacuo. The residue was taken up in EtOAc (600 ml.) from which a tar precipitated. The solution was treated with decolourising carbon, filtered and evaporated to give 4-amino-2-chloromethylpyrimidine as a brown solid.

The above pyrimidine (1.4 g.) and thiourea (0.8 g.) in EtOH (40 ml.) were heated under reflux for 20 minutes, a crystalline precipitate being formed. On cooling S-[4-aminopyrimid-2-ylmethyl]isothiourea hydrochloride was isolated by filtration.

The above isothiourea (2 g.) was added to a solution of potassium hydroxide (1.1 g.) in water (20 ml.) and the solution stirred for 2 hours under nitrogen. Acrylonitrile (1 ml.) was then added and the mixture vigorously stirred for 30 minutes. The solution was extracted with EtOAc, the extract dried (MgSO$_4$) and evaporated in vacuo to give 3-[4-aminopyrimid-2-ylmethylthio]propionitrile as a gum which solidified on standing, m.p. 106°–9°.

To a solution of 3-(4-aminopyrimid-2-ylmethylthio)-propionitrile (1.7 g.) in acetonitrile (40 ml.) was added 2,2,2-trifluoroethylisothiocyanate (2 ml.) and the solution heated under reflux for 17 hours. The acetonitrile was evaporated in vacuo and the residue dissolved in EtOAc, treated with decolourising carbon, filtered and evaporated to give 3-[4-(3-[2,2,2-trifluoroethyl]thioureido)pyrimid-2-ylmethylthio]propionitrile as an orange solid, m.p. 108°–110°.

The above thiourea (1 g.) in DMF (10 ml.) and 8 M ammonia in EtOH (10 ml.) was treated with mercuric oxide (3 g.). The mixture was stirred for 40 minutes, diluted with EtOAc/water 1:1 v/v (100 ml.) and filtered through diatomaceous earth. The EtOAc extract was dried (MgSO$_4$) and evaporated in vacuo to give 3-[4-(2-[2,2,2-trifluoroethyl]guanidino)pyrimid-2-ylmethylthio]propionitrile as an oil, which was used without further purification.

EXAMPLE 47

The process described in Example 46 was repeated, using 4-[4-(2-[2,2,2-trifluoroethyl]guanidino)pyrimid-2-ylmethylthio]butyronitrile, to give 4-[4-(2-[2,2,2-trifluoroethyl]guanidino)pyrimid-2-ylmethylthio]butyramide, m.p. 126°–128° (yield 45%).

The starting material may be prepared by repeating the fourth, fifth and sixth parts of Example 46 using 4-bromobutyronitrile in place of acrylonitrile.

EXAMPLE 48

A solution of trans-6-[4-(2-[2,2,2-trifluoroethyl]-guanidino)pyrimid-2-yl]hex-5-enenitrile (400 mg.) in concentrated sulphuric acid (2 ml.) was kept at 20° for 18 hours then added dropwise to saturated aqueous sodium carbonate. The mixture was extracted with EtOAc (2×15 ml.) and the extract dried (MgSO$_4$) and evaporated in vacuo to give trans-6-[4-(2-[2,2,2-trifluoroethyl]guanidino)pyrimid-2-yl]hex-5-enamide as an oil. The maleic acid salt was prepared in acetone (yield 205 mg; 36%), m.p. 177°–179°.

The starting material may be prepared as follows:

To a solution of thiophenol (50 ml.) in 2.5 M aqueous sodium hydroxide (400 ml.) stirred under nitrogen at 20° was added chloroacetamidine hydrochloride (63 g.) in water (250 ml.). The precipitated solid was collected, pressed dry, suspended in EtOAc and the EtOAc evaporated. The solid was resuspended in EtOAc, a saturated solution of hydrochloric acid in EtOAc added and the mixture stirred for 30 minutes. The hydrochloride salt of phenylthioacetamide was collected, washed with ether and used directly.

Phenylthioacetamidine hydrochloride (10 g.), 2-chloroacrylonitrile (8.75 g.), triethylamine (27.5 ml.) and EtOH (75 ml.) were heated under reflux together for 4 hours. The solution was evaporated in vacuo and the residue partitioned between EtOAc and 1 M aqueous hydrochloric acid. The aqueous extract was basified and extracted with EtOAc (3×100 ml.), dried (MgSO$_4$) and evaporated in vacuo to give a red oil containing 4-amino-2-phenylthiomethylpyrimidine.

The crude 4-amino-2-phenylthiomethylpyrimidine (15 g.) in MeOH (150 ml.) and water (100 ml.) at 60° was treated over 15 minutes with sodium metaperiodate (20 g.) in water (100 ml.). The MeOH was evaporated in vacuo and the clear aqueous solution decanted from the red gum which precipitated. 4-Amino-2-phenylsulphinylmethylpyrimidine crystallised from the aqueous solution as a white solid, m.p. 202°–204°. Recrystallisation from EtOH/ether gave an analytical sample, m.p. 207°–208°.

To a solution of potassium t-butoxide (0.88 g.) in DMF (30 ml.) stirred at 0° under nitrogen was added 4-amino-2-phenylsulphinylmethylpyrimidine (1.84 g.). The solution was stirred for 10 minutes and 5-bromovaleronitrile (1.3 g.) in DMF (5 ml.) added over 5 minutes. The mixture was stirred for 30 minutes at 0°, poured into water (150 ml.) and extracted with EtOAc (4×15 ml.) and the extract dried (MgSO$_4$) and evaporated in vacuo to give a clear gum (1.7 g.). The gum was heated in toluene (40 ml.) at reflux for 30 minutes during which time it dissolved. The toluene was evaporated in vacuo and the residue partitioned between CH$_2$Cl$_2$ and 1 M aqueous hydrochloric acid. The aqueous layer was basified with 4 M aqueous sodium hydroxide and extracted with CH$_2$Cl$_2$ (3×15 ml.), the extract dried (MgSO$_4$) and evaporated in vacuo to give a clear gum (900 mg.). To this gum (900 mg.) in acetonitrile (20 ml.) was added 2,2,2-trifluoroethylisothiocyanate (500 ml.) and the solution heated under reflux for 19 hours. The acetonitrile was evaporated in vacuo and trans-6-[4-(3-[2,2,2-trifluoroethyl]thioureido)pyrimid-2-yl]hex-5-enenitrile was isolated from the mixture by medium pressure chromatography on silica using EtOAc/cyclohexane 3:7 v/v as eluant.

The above thiourea (350 mg.) was dissolved in DMF (8 ml.) and 8 M ammonia in EtOH (4 ml.). Mercuric oxide (1 g.) was added and the mixture stirred for 40 minutes, then poured into water/EtOAc 1:1 (100 ml.) and the resulting mixture filtered through diatomaceous earth. The EtOAc extract was dried (MgSO$_4$) and evaporated in vacuo to give trans-6-8 4-(2-[2,2,2-trifluoroethyl]guanidino)pyrimid-2-yl]hex-5-enenitrile as a gum which was used without further purification.

EXAMPLE 49

Methyl 3-[2-(2-[2,2,2-trifluoroethyl]guanidino)-thiazol-4-ylmethylthio]propionate (0.5 g.) in EtOH (20 ml.) was treated with 33% w/v ethanolic methylamine (7 ml.) and stirred for 18 hours at room temperature. The solution was evaporated and the residue crystallised from aqueous EtOH to give N-methyl-3-[2-(2-[2,2,2-trifluoroethyl]guanidino)thiazol-4-ylmethylthio]-propionamide (0.35 g.), m.p. 152°–154° (73%).

The starting material may be prepared as follows:

A mixture of 2-[2,2,2-trifluoroethyl]guanidino-4-chloromethylthiazole hydrochloride (4.6 g.) in EtOH (75 ml.) and methyl 3-mercaptopropionate (2.47 ml.) at 5° was treated dropwise with aqueous sodium hydroxide (1.8 g. in 15 ml. of water) over 10 minutes. The resulting solution was allowed to reach room temperature and was stirred for 1 hour. It was then poured into water and the precipitate filtered and crystallised from EtOH to give methyl 3-[2-(2-[2,2,2-trifluoroethyl]-guanidino)thiazol-4-ylmethylthio]propionate (1.93 g), m.p. 96°–98°.

EXAMPLE 50

The process of Example 49 was repeated, using the appropriate starting materials, to give 3-(2-[2-(2,2,2-trifluoroethyl)guanidino]thiazol-4-yl)propionic acid hydrazide, m.p. 125°–126° (yield 69%).

EXAMPLE 51

A mixture of methyl 5-[2-(2-[2,2,2-trifluoroethyl]-guanidino)thiazol-4-yl]valerate (0.4 g.) and ethanolic methylamine (33% w/v, 60 ml.) was allowed to stand at room temperature for 2 days. The mixture was then evaporated to dryness and the residue recrystallised from EtOAc/ether to give N-methyl-5-[2-(2-[2,2,2-trifluoroethyl]guanidino)thiazol-4-yl]valeramide (yield 85%), m.p. 122°–126°.

The starting material may be prepared as follows:

To a solution of methyl 7-chloro-6-oxoheptanoate (2.0 g.) in hot EtOH (20 ml.) was added a solution of 2,2,2-trifluoroethylamidinothiourea (2.1 g.) in hot EtOH (20 ml.). The resulting mixture was heated under reflux for 1 hour. The mixture was then evaporated to dryness and the residue partitioned between ether (20 ml.) and water (60 ml.). The aqueous layer was separated and basified with sodium bicarbonate and extracted with EtOAc. The EtOAc solution was evaporated to dryness and the residue crystallised from EtOAc/ether containing a small amount of acetone to give methyl 5-[2-(2-[2,2,2-trifluoroethyl]guanidino)-thiazol-4-yl]valerate which was used without further purification.

EXAMPLE 52

The process of Example 51 was repeated, using the appropriate starting material, to give N-methyl 4-[2-(2-

[2,2,2-trifluoroethyl]guanidino)thiazol-4-yl]butyramide. Requires C, 47.1%, H, 6.9%, N, 26.8%. Found C, 47.0%, H, 6.7%; N, 26.8%.

The starting material may be prepared by repeating the second part of Example 51 using methyl 6-chloro-5-oxohexanoate in place of methyl 7-chloro-6-oxoheptanoate to give methyl 4-[2-(2-[2,2,2-trifluoroethyl]-guanidino)thiazol-4-yl]butanoate.

EXAMPLE 53

A solution of methyl 3-[2-(2-[2,2,2-trifluoroethyl]-guanidino)thiazol-4-yl]cyclopentanecarboxylate (0.25 g.) in ethanolic methylamine (33% w/v, 50 ml.) was allowed to stand at room temperature for 5 days. The solution was then evaporated to dryness and the residue in acetone treated with maleic acid to give N-methyl-3-[2-(2-[2,2,2-trifluoroethyl]guanidino)thiazol-4-yl]cyclopentanecarboxamide hydrogen maleate (yield 63%), m.p. 156°–158°.

The starting material may be prepared as follows:

A mixture of cyclopentane-1,3-dicarboxylic acid mono methyl ester (18.6 g.) and thionyl chloride (50 ml.) was allowed to stand at room temperature for 3 hours. The mixture was then evaporated to dryness and the residue twice evaporated to dryness from a toluene solution. The residue was added to an excess of diazomethane solution in ether and the mixture allowed to stand at room temperature for 18 hours and then evaporated to dryness. The residue was dissolved in acetone (100 ml.) and concentrated hydrochloric acid was added slowly until evolution of nitrogen ceased. The resulting mixture was evaporated to low bulk and partitioned between EtOAc and aqueous sodium bicarbonate. The EtOAc layer was separated, dried and evaporated to dryness to give methyl 3-[2-chloro-1-oxoethyl]-cyclopentanecarboxylate as a brown oil (16 g.).

A solution of this material (3.0 g.) in EtOH (20 ml.) was added to a solution of 2,2,2-trifluoroethylamidinothiourea (2.8 g.) in EtOH (20 ml.). The mixture was heated under reflux for 2 hours and then evaporated to dryness. The residue was partitioned between water (40 ml.) and EtOAc (60 ml.). The aqueous layer was basified with sodium bicarbonate and the precipitate extracted into EtOAc. This was evaporated to dryness and the residue obtained purified by preparative thin layer chromatography using CHCl3/MeOH/aqueous ammonia (s.g. 0.880) 90:10:0.1 v/v/v as eluant. The appropriate band was isolated to give methyl 3-[2-(2-[2,2,2-trifluoroethyl]guanidino)thiazol-4-yl]cyclopentanecarboxylate (0.64 g.) as a gum which was used without further purification.

EXAMPLE 54

A solution of crude methyl 3-[2-(2-[2,2,2-trifluoroethyl]guanidino)thiazol-4-yl]benzoate hydrochloride (1 g.) in ethanolic methylamine (33% w/v, 20 ml.) was allowed to stand at room temperature for 4 days. The mixture was then evaporated to dryness and the residue triturated with water to give 0.16 g. of N-methyl-3-[2-(2-[2,2,2-trifluoroethyl]guanidino)thiazol-4-yl]benzamide (yield 20%). The n.m.r. spectrum in d6DMSO included the following resonances: 2.8 (d, 3H); 4.1 (m, 2H); 7.3 (s, 1H); 7.0–8.4 (complex, 7H).

The starting material may be prepared as follows:

A solution of 3-cyanophenacyl chloride (3.6 g.) in warm EtOH (30 ml.) was added to a solution of 2,2,2-trifluoroethylamidinothiourea (4.0 g.) in EtOH (30 ml.). The mixture was then heated under reflux for 1 hour and evaporated to low volume. On cooling this solution deposited 3-[2-(2-[2,2,2-trifluoroethyl]guanidino)-thiazol-4-yl]benzonitrile hydrochloride (4.4 g.). The n.m.r. in d6DMSO included the following resonances: 4.4 (m, 2H); 7.5–9.2 (complex, 8H).

The above material (4.3 g.) was heated under reflux in a mixture of HOAC (30 ml.) and concentrated aqueous HCl (30 ml.) for 2 hours. The solution was then evaporated to dryness and the residue dissolved in MeOH (100 ml.). To this was added thionyl chloride (20 ml.) dropwise. The solution was then evaporated to dryness to give crude methyl 3-[2-(2-[2,2,2-trifluoroethyl]-guanidino)thiazol-4-yl]benzoate hydrochloride which was used without further purification.

EXAMPLE 55

A solution of 5-[3-(2-[2,2,2-trifluoroethyl]guanidino)-1,2,4-triazol-1-yl]valeronitrile (0.15 g.) in concentrated sulphuric acid (3 ml.) was stirred for 1.5 hours at room temperature then poured onto ice and basified with concentrated aqueous ammonia. Extraction with EtOAc gave 0.12 g. of a white solid which was triturated with ether to give 5-[3-(2-]2,2,2-trifluoroethyl]-guanidino)-1,2,4-triazol-1-yl]valeramide (0.085 g., 54%), m.p. 162°–164°.

The starting material may be prepared as follows:

3-Amino-1,2,4-triazole (4.2 g.) was added to a solution of sodium methoxide in MeOH (1.2 g. sodium in 30 ml. MeOH) and the solution stirred for 0.5 hours at room temperature. 5-Bromovaleronitrile (8.1 g.) was added and the solution heated under reflux for 12 hours. The solution was evaporated and the residue partitioned between water and EtOAc. The extracts were washed with brine, dried over MgSO4 and evaporated to give a pale yellow oil (6.5 g.) which was purified by medium pressure liquid chromatography using EtOAc/MeOH 6:1 v/v as eluant. The colourless oil obtained was used without characterisation for the following reaction. The crude 1-(4-cyanobutyl)-3-amino-1,2,4-triazole (5.45 g.) in acetonitrile (80 ml.) was treated with 2,2,2-trifluoroethylisothiocyanate (4.4 g.) and the solution heated under reflux for 3.5 hours. Evaporation gave a white sticky solid which was triturated with ether/EtOH to give 5-(3-[3-(2,2,2-trifluoroethyl)thioureido]-1,2,4-triazol-1-yl)valeronitrile (4.04 g.) as a white solid, m.p. 136°–138°.

This nitrile (3.6 g.) in MeOH (80 ml.) and acetonitrile (5 ml.) was treated with mercuric oxide (3.06 g.) and methanolic ammonia (15 ml.). After stirring for 1.5 hours the black suspension was filtered through diatomaceous earth and the filtrates evaporated to give a white solid. The solid was washed with ether and filtered to give 5-[3-(2-[2,2,2-trifluoroethyl]guanidino)-1,2,4-triazol-1-yl]valeronitrile (2.87 g.) as a white solid, m.p. 200°–201° after recrystallisation from EtOH.

EXAMPLE 56

A solution of 5-[4-(2-[2,2,2-trifluoroethyl]guanidino)-1,3,5-triazin-2-ylthio]valeronitrile (0.25 g.) in concentrated sulphuric acid (1 ml.) was kept at room temperature for 4 hours. The reaction mixture was diluted with an equal volume of ice, basified with aqueous NaOH and then filtered to give a white solid. This solid was dissolved in a small volume of EtOH and acetone and treated with a solution of maleic acid (0.09 g.) in a small volume of acetone. The mixture was left at room temperature overnight and then filtered to give 0.15 g. of 5-[4-(2-[2,2,2-trifluoroethyl]guanidino)-1,3,5-triazin-2- ylthio]valeramide maleate, m.p. 166°–168° after recrystallisation from EtOH.

The starting material may be prepared as follows:

A stirred mixture of 2-mercapto-4-amino-1,3,5-triazine (5.1 g.), 10% w/v aqueous NaOH (16 ml.) and 5-bromovaleronitrile was kept at room temperature for 3 hours. The mixture was filtered to separate a first crop of product. The filtrate was kept at room temperature overnight and refiltered to yield another crop of product. These crops were washed with ether and recrystallised from EtOH to give 6.7 g. of 5-(4-amino-1,3,5-triazin-2-ylthio)valeronitrile, m.p. 123°–125°.

A stirred mixture of 5-(4-amino-1,3,5-triazin-2-ylthio)valeronitrile (0.9 g.) and THF (30 ml.) was kept under argon at −60° and treated with a solution of n-butyllithium in hexane (1.6 M; 3.1 ml.). The mixture was stirred at −60° for 30 minutes and then treated with 2,2,2-trifluoroethylisothiocyanate (0.7 g.). The mixture was allowed to warm to room temperature and stirred overnight. The mixture was poured into water and acidified with a small volume of concentrated hydrochloric acid. The aqueous and organic phases were separated. The aqueous phase was extracted with EtOAc and the extract was combined with the organic phase from the reaction mixture. The combination was dried (MgSO$_4$) and evaporated to give a sticky solid that was triturated with petroleum ether (b.p. 40°–60°) and EtOAc and filtered to give 1.0 g. of 5-[4-(3-[2,2,2-trifluoroethyl]thioureido)-1,3,5-triazin-2-ylthio]valeronitrile, m.p. 136°–137° after recrystallisation from EtOH.

A stirred suspension of 5-[4-(3-[2,2,2-trifluoroethyl]thioureido)-1,3,5-triazin-2-ylthio]valeronitrile (2.0 g.) in ammoniacal EtOH (6 M; 40 ml.) was treated at room temperature with mercuric oxide (2.0 g.). After about 1 hour the mixture was diluted with DMF (20 ml.). The mixture was kept at room temperature overnight, filtered, and evaporated. The non-volatile residue was dissolved in DMF (40 ml.) and ammoniacal EtOH (6 M; 20 ml.) and treated at room temperature with mercuric oxide (1 g.). The mixture was stirred for 4 hours and then filtered. The filtrate was evaporated to dryness, redissolved in EtOH and saturated with H$_2$S gas. The mixture was filtered, evaporated to dryness, redissolved in EtOAc (15 ml.), refiltered, treated with a solution of maleic acid (0.66 g.) in a small volume of acetone, and then diluted with petroleum ether (b.p. 60°–80°) to give a solution from which the product gradually precipitated. The precipitate was filtered, washed with a small volume of cold acetone and then with petroleum ether (b.p. 60°–80°) to give 1.6 g. of 5-[4-(2-[2,2,2-trifluoroethyl]guanidino)-1,3,5-triazin-2-ylthio]valeronitrile maleate, m.p. 155°–156° after recrystallisation from EtOH.

EXAMPLE 57

To a solution of 4-(2-[3-(2-[2,2,2-trifluoroethyl]guanidino)pyrazol-1-yl]ethoxymethyl)benzonitrile (650 mg.) in MeOH (5 ml.) was added hydrogen peroxide (30%, 100 volume) (2 ml.) followed by N aqueous NaOH (1 ml.). The mixture was then stirred at room temperature for 2.25 hours. The solvent was then evaporated in vacuo to give a yellow gum (700 mg.). This gum was purified by medium pressure chromatography using EtOAc/EtOH/triethylamine 96:3:1 v/v/v as eluant to give 4-(2-[3-(2-[2,2,2-trifluoroethyl]guanidino)pyrazol-1-yl]ethoxymethyl)benzonitrile (210 mg.; 31%) having the following n.m.r. in d$_6$DMSO: 7.5 (m, 4H); 7.5 (d, 1H); 5.8 (d, 1H); 5.0 (s, 2H); 4.0 (m, 4H); 3.7 (m, 2H).

The starting material may be prepared as follows:

2-Hydroxyethylhydrazine (7.6 g.) was added slowly to a solution of potassium carbonate (13.8 g.) in water (40 ml.). The mixture was cooled to 0°, then 2-chloroacrylonitrile (8.75 g.) was added slowly with vigorous stirring. Stirring was continued for a further 17 hours and the mixture was then continuously extracted with EtOAc for 20 hours. On evaporation of the solvent, 3-amino-1-(2-hydroxyethyl)pyrazole was obtained, (7.7 g.; 60%), b.p. 170°/0.5 mm.

A solution of 2,2,2-trifluoroethylisothiocyanate (13.8 g.) and 3-amino-1-(2-hydroxyethyl)pyrazole (12.5 g.) in acetonitrile dried over 4A molecular sieve (30 ml.) was stirred at room temperature for 4 hours. A precipitate formed after 30 minutes. Filtration gave 1-(2-hydroxyethyl)-3-[3-(2,2,2-trifluoroethyl)thioureido]pyrazole (12.1 g.; 46%), m.p. 145°–146°.

To a solution of 1-(2-hydroxyethyl)-3-[3-(2,2,2-trifluoroethyl)thioureido]pyrazole (20.0 g.) in 5 N ammonia in EtOH solution (700 ml.) was added yellow mercuric oxide (64.8 g.) with stirring. Stirring was continued for a period of 2 hours. The mixture was filtered through diatomaceous earth and the solvent then evaporated to dryness in vacuo. The residual oil was triturated with ether to give 1-(2-hydroxyethyl)-3-[2-(2,2,2-trifluoroethyl)guanidino]pyrazole (18.5 g.; 99%), m.p. 82°.

A mixture of 1-(2-hydroxyethyl)-3-[2-(2,2,2-trifluoroethyl)guanidino]pyrazole (2.51 g.) and p-cyanobenzyl bromide (1.96 g.) was heated at 140° for 10 minutes. The melt, on cooling, was dissolved in MeOH (5 ml.) and purified by chromatography on silica gel using EtOAc/EtOH/triethylamine 9:1:1 v/v/v as eluant to give 4-(2-[3-(2-[2,2,2-trifluoroethyl]guanidino)pyrazol-1-yl]ethoxymethyl)benzonitrile (700 mg.; 19%).

EXAMPLE 58

To a solution of 4-(3-[3-(2,2,2-trifluoroethyl)thioureido]pyrazol-1-ylmethyl)benzamide (180 mg.) in EtOH saturated with ammonia (5 ml.) was added yellow mercuric oxide (380 mg.). The mixture was stirred at room temperature for 17 hours. The mixture was centrifuged, then the supernatant liquor was evaporated in vacuo to give 4-[3-(2-[2,2,2-trifluoroethyl]guanidino)-pyrazol-1-ylmethyl]benzamide, m.p. 192° (from EtOH/petroleum ether (b.p. 60°–80°)).

The starting material may be prepared as follows:

Sodium hydride paste (61% w/w dispersion in oil, 70 mg.) was added to a solution of 3-nitropyrazole (200 mg.) in dry DMF (2.5 ml.) with stirring. When effervescence had ceased, 4-chloromethylbenzamide (300 mg.) was added. The mixture was stirred at room temperature for 2 days, then diluted with water (20 ml.). The precipitated 4-[3-nitropyrazol-1-ylmethyl]benzamide (300 mg.), m.p. 200°–201°, was collected by filtration.

A solution of the above nitro amide (100 mg.) in dry DMF was hydrogenated at room temperature and at atmospheric pressure using 5% w/w palladium on carbon (10 mg.) as catalyst. Filtration and subsequent evaporation in vacuo of the filtrate gave 4-[3-aminopyrazol-1-ylmethyl]benzamide.

A mixture of the above amine (250 mg.) and 2,2,2-trifluoroethylisothiocyanate (0.16 g.) in acetonitrile (1 ml.) was stirred at room temperature for 3 hours. The precipitated solid was filtered off to give 4-(3-[3-(2,2,2-trifluoroethyl)thioureido]pyrazol-1-ylmethyl)benzamide (180 mg.), m.p. 205°–206°.

EXAMPLE 59

A solution of 4-[6-(2-[2,2,2-trifluoroethyl]guanidino)-pyrid-2-ylthio]butyric acid (84 mg.) and triethylamine (0.2 ml.) in DMF (5 ml.) was stirred at 0° while isobutylchloroformate (68 mg.) was added. The solution was kept at 0° for 0.5 hours, treated with a saturated solution of ammonia in EtOH (1 ml.) and then stirred at room temperature for 18 hours. The solution was evaporated to dryness and the residue partitioned between N aqueous HCl and EtOAc. The aqueous phase was basified with 10 N aqueous NaOH and extracted with EtOAc, and the extract was dried and evaporated to dryness to give 4-[6-(2-[2,2,2-trifluoroethyl]guanidino)pyrid-2-ylthio]butyramide (60 mg.) which was crystallised as the hydrogen maleate salt from acetone, m.p. 138°–141°.

The starting material may be prepared as follows:

A mixture of 4-mercaptobutyric acid (0.72 g.) a 50% w/w dispersion of sodium hydride in mineral oil (0.58 g.) and 2-ethoxyethanol (5 ml.) was treated with 2-amino-6-bromopyridine (0.35 g.) and the mixture was heated under reflux for 18 hours and then evaporated to dryness. The residue was partitioned between water and EtOAc and the aqueous phase was neutralised with HOAc. The precipitated yellow solid was collected to give 4-(6-aminopyrid-2-ylthio)butyric acid (0.27 g.) which was used without further purification.

A mixture of 4-(6-aminopyrid-2-ylthio)butyric acid (0.21 g.), DMF (3 ml.) and 2,2,2-trifluoroethylisothiocyanate (0.15 g.) was left at room temperature for 18 hours and then evaporated to dryness. A solution of the residue in methanolic ammonia was treated with yellow mercuric oxide (0.43 g.) and the mixture stirred at room temperature for 1 hour. The mixture was filtered and the filtrate evaporated to dryness and the residue treated with 2 N aqueous NaOH (5 ml.) and then filtered. The filtrate was acidified with HOAc and the precipitate collected to give 4-[6-(2-[2,2,2-trifluoroethyl]guanidino)pyrid-2-ylthio]butyric acid (0.17 g.) which was used without further purification.

EXAMPLE 60

The process of Example 59 was repeated, using the appropriate starting material, to give 5-[6-(2-[2,2,2-trifluoroethyl]guanidino)pyrid-2-ylthio]valeramide maleate, m.p. 138°–139° (yield 69%).

The starting material may be prepared by repeating the second and third parts of Example 59 using 5-mercaptovaleric acid in place of 4-mercaptobutyric acid to give 5-[6-(2-[2,2,2-trifluoroethyl]guanidino)pyrid-2-ylthio]valeric acid.

EXAMPLE 61

A solution of 4-[6-(2[2,2,2-trifluoroethyl]guanidino)-pyrid-2-yloxy]butyronitrile (0.2 g.) in concentrated sulphuric acid was kept at room temperature for 6 hours and then diluted with water and basified with 10 N aqueous NaOH. The solution was extracted three times with EtOAc, and the combined extracts dried and evaporated to dryness. A solution of the residue in acetone was added to a solution of maleic acid in acetone, and the crystalline precipitate was collected to give 4-[6-(2-[2,2,2-trifluoroethyl]guanidino)pyrid-2-yloxy]butyramide hydrogen maleate (0.14 g.), m.p. 176°–177°.

The nitrile used as starting material may be prepared as follows:

A mixture of 4-hydroxybutyronitrile (0.85 g.), a 50% w/w dispersion of sodium hydride in mineral oil (0.48 g.) and sulpholane (5 ml.) was stirred at room temperature for 1 hour. The mixture was treated with 2-amino-6-bromopyridine (0.87 g.) and the mixture heated with stirring at 130° for 18 hours. The cooled mixture was diluted with water (20 ml.), acidified with concentrated aqueous HCl and washed with ether. The aqueous phase was basified with 10 N aqueous NaOH, extracted three times with EtOAc and the combined extracts dried and evaporated to dryness.

A solution of the residue in acetonitrile (5 ml.) was treated with 2,2,2-trifluoroethylisothiocyanate, and the solution heated under reflux for 1 hour and then evaporated to dryness. The residue was stirred with 2 N aqueous HCl (20 ml.) and ether (20 ml.) and the insoluble material collected.

The solid was dissolved in methanolic ammonia solution, and the solution treated with yellow mercuric oxide (2 g.) and then stirred at room temperature for 18 hours. The mixture was filtered and the filtrate evaporated to dryness to give 4-[6-(2-[2,2,2-trifluoroethyl]guanidino)pyrid-2-yloxy]butyronitrile (1.0 g.) which was used without further purification.

EXAMPLE 62

In a similar manner to the process described in Example 61, using 4-[2-(2-[2,2,3,3-tetrafluoropropyl]guanidino)pyrid-6-ylthio]butyronitrile as starting material, there was obtained 4-[2-(2-[2,2,3,3-tetrafluoropropyl]guanidino)pyrid-6-ylthio]butyramide maleate, m.p. 173°–174° (yield 58%).

The above nitrile may be prepared in an analogous manner to the butyric acid described in Example 59, using 4-mercaptobutyronitrile in place of 4-mercaptobutyric acid and 2,2,3,3-tetrafluoropropylisothiocyanate in place of 2,2,2-trifluoroethylisothiocyanate.

EXAMPLE 63

A mixture of 5-(3-aminopyrazol-1-yl)valeramide (18.2 mg.) and (2,2,2-trifluoroethyl)-S-methylisothiourea hydroiodide (51 mg.) was heated at 100° for 20 minutes. Preparative high pressure liquid chromatography on silica gel, using CHCl$_3$/MeOH/ammonia (s.g. 0.880) 8:2:0.5 v/v/v as eluant gave 5-[3-(2-[2,2,2-trifluoroethyl]guanidino)pyrazol-1-yl]valeramide, m.p. 129°–130° (40%).

The isothiourea used as starting material may be prepared as follows:

A solution of ammonium thiocyanate (9.12 g.), and 2,2,2-trifluoroethylamine hydrochloride (13.6 g.) in water (50 ml.) was heated at 100° for 20 hours. Water (50 ml.) was added and the mixture reheated to redissolve the solid. On cooling crystals of 2,2,2-trifluoroethylthiourea hydrate, m.p. 154°–156° (52.4%), were precipitated.

A solution of 2,2,2-trifluoroethylthiourea (8.0 g.) and methyl iodide (3.5 g.) in EtOH (40 ml.) was heated under reflux for 70 minutes, then evaporated to dryness in vacuo. The residue was triturated with ether to give 2,2,2-trifluoroethyl-S-methylisothiourea hydroiodide, m.p. 154°–156° (90%).

EXAMPLE 64

A tablet containing 50 mg. of 5-[3-(2-[2,2,3,3-tetrafluoropropyl]guanidino)pyrazol-1-yl]valeramide may be prepared using ingredients in the following proportions:

|   |   | mg./tablet |
|---|---|---|
| (a) | Tablet Core. | |
|   | Active agent | 50 |
|   | Lactose | 218.5 |
|   | Calcium carboxymethylcellulose | 22.5 |
|   | Polyvinylpyrrolidone | 6.0 |
|   | Magnesium stearate | 3.0 |
| (b) | Tablet Coat | |
|   | Hydroxypropylmethylcellulose | 4.5 |
|   | Polyethylene glycol | 0.9 |
|   | Titanium dioxide | 1.35 |

The active agent, lactose and calcium carboxymethylcellulose are mixed. An aqueous solution of polyvinylpyrrolidone is added, and the mass is then mixed until it is suitable for granulation. The mass is then granulated and dried. The magnesium stearate is blended with the dried granules and the resulting mixture is compressed into tablets. The tablets are film-coated using an aqueous or solvent suspension of hydroxypropylmethylcellulose, polyethylene glycol and titanium dioxide.

We claim:

1. A guanidine derivative of the formula I:

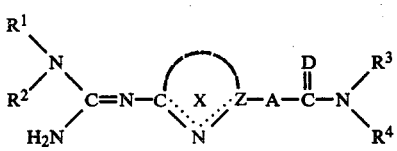

in which $R^1$ and $R^2$, which may be the same or different, are hydrogen or branched or unbranched 1-10C alkyl, 3-8C cycloalkyl or 4-14C cycloalkylalkyls, each alkyl, cycloalkyl or cycloalkylalkyl being optionally substituted by one or more halogens selected from fluorine, chlorine and bromine, provided that at least one of $R^1$ and $R^2$ is a halogen-substituted alkyl, cycloalkyl or cycloalkylalkyl, and provided that there is no halogen substituent on the carbon of the alkyl, cycloalkyl or cycloalkylalkyl which is directly attached to the nitrogen atom;

in ring X is selected from oxazole, thiazole, imidazole, 1,2,4-thiadiazole, 1,2,4-oxadiazole, 1,2,3-triazole, 1,2,4-triazole and pyrazole, and which heterocyclic ring may, where possible, carry one or two optional substituents, the optional substituents on ring X being selected from fluorine, chlorine, bromine, 1-6C alkyl, 1-6C alkoxy, trifuloromethyl, hydroxy and amino radicals; —A— is a phenylene or 5-7C cycloalkylene radical or a 1-8C alkylene chain which is optionally substituted by one or two 1-3C alkyls radicals and into which is optionally inserted, as part of the backbone of the chain, one or two groups selected from oxygen and sulphur atoms and NH, 1-6C N-alkyl, cis and trans vinylene, ethynylene, phenylene and 5-7C cycloalkylene radicals, provided that the shortest link between ring X and C=D is of at least 3 atoms, provided that when an optional insertion is made in chain A which results in the inserted group being directly attached to C=D the inserted group is other than an oxygen or sulphur atom or an NH or N-alkyl radical, and provided that no two insertions selected from oxygen and sulphur atoms and NH and N-alkyl radicals are directly attached one to the other;

D is an oxygen or sulphur atom;

$R^3$ is a hydrogen atom or a hydroxy, amino, 1-6C alkylamino, 1-C haloalkylamino, 1-6C alkanoylamino, 1-6C alkyl, 3-8C cycloalkyl, 4-12C cycloalkylalkyl, 2-6C alkenyl, 2-6C alkynyl, 1-6C haloalkyl, 1-6C alkoxy, 1-6C hydroxyalkyl, 2-10C alkoxyalkyl, 2-10C alkylthioalkyl, 1-6C aminoalkyl, 2-8C alkylaminoalkyl, 3-12C dialkylaminoalkyl, 2-8C alkanoylaminoalkyl, 8-14C benzoylaminoalkyl, 3-10C alkoxycarbonylalkyl, 2-8C carbamoylalkyl, phenyl, 7-11C phenylalkyl, heteroaryl or heteroarylalkyl radicals, wherein the heteroaryl part is a furan, thiophene, pyrrole, thiazole, oxazole, imidazole, thiadiazole, oxadiazole, triazole, pyrazole, pyridine or pyrimidine ring, wherein the alkyl part of the heteroarylalkyl radical is 1-6C and wherein, when $R^3$ is or contains a phenyl or heteroaryl ring, that ring is optionally substituted by one or two groups selected from fluorine, chlorine, bromine and iodine atoms and 1-6C alkyl, 1-6C alkoxy, 1-6C alkylthio, 2-6C dialkylamino, 2-6C alkanoyl, trifluoromethyl, hydroxy and amino radicals; $R^4$ is a hydrogen atom or $R^3$ and $R^4$ are joined to form, together with the nitrogen atom to which they are attached, a pyrrolidine, piperidine, morpholine, pipevazine or N-methylpiperazine ring;

and the pharmaceutically-acceptable acid-addition salts thereof.

2. A guanidine derivative of the formula I given in claim 1 in which $R^1$ and $R^2$ are selected from the group consisting of hydrogen atoms, and 2,2,2-trifluoroethyl, 2,2,2-trichloroethyl, 2-chloro-2,2-difluoroethyl, 2,2-dichloro-2-fluoroethyl, 2-bromo-2,2-difluoroethyl, 2,2-dibromo-2-fluoroethyl, 2-fluoroethyl, 2-chloroethyl, 2,2-difluoroethyl, 2,2-dichloroethyl, 2-chloro-2-fluoroethyl, 2-bromo-2-fluoroethyl, 2,2,3,3-tetrafluoropropyl, 2,2,3,3,3-pentafluoropropyl, 1,1,1,3,3,3-hexafluoroisopropyl, 1,3-dichloro-1,1,3,3-tetrafluoroisopropyl, 1-chloro-1,1,3,3,3-pentafluoroisopropyl, 1,3-difluoroisopropyl, 2,2,3,3,4,4,4-heptafluorobutyl, 2,2,3,3-tetrafluorocyclopropyl, 2-chloro-2,3,3-trifluorocyclopropyl, 2,2-difluorocyclopropyl, 2-chloro-3,3-difluorocyclopropyl, 2,2,3,3,4,4-hexafluorocyclobutyl, 2-chloro-2,3,3,4,4-pentafluorocyclobutyl, (1,2,2,3,3-pentafluorocyclopropyl)methyl, (2-chloro-1,2,3,3-tetrafluorocyclopropyl)methyl, (1,2,2,3,3,4,4-heptafluorocyclobutyl)methyl, (2-chloro-1,2,3,3,4,4-hexafluorocyclobutyl)methyl, methyl, ethyl, propyl, isopropyl, butyl, cyclopropyl, cyclobutyl, cyclopropylmethyl and cyclopropylbutyl radicals provided that at least one of $R^1$ and $R^2$ is a halogen-substituted radical; the optional substituents on ring X are selected from fluorine, chlorine, bromine, methyl, methoxy methylthio, trifluoromethyl, hydroxy and amino radicals; —A— is a phenylene, cyclopentylene, cyclohexylene, trimethylene, tetramethylene, pentamethylene, thioethylene, thiotrimethylene, thiotetramethylene, thiopentamethylene, oxyethylene, oxytrimethylene, oxytetramethylene, methylenethiomethylene, methylenethioethylene, methylenethiopropylene, methyleneoxymethylene, methyleneoxyethylene, ethyleneoxyethylene, oxy-2-methylethylene, thiopropylenethiomethylene, oxyethyleneoxymethylene, iminopropylene, iminoethylene, vinylenepropylene, oxymethylene-vinylene, 1,3-phenylene, 1,3-cyclopentylene, methylene-1,4-phenylene, ethyleneoxymethylene-1,4-phenylene, oxy-1,3-phenylenemethylene or thiomethyleneethynylenemethylene radical;

D is an oxygen or sulphur atom;

$R^3$ is a hydrogen atom or a hydroxy, amino, methylamino, 2,2,2-trifluoroethylamino, acetylamino, methyl, cyclohexyl, cyclohexylmethyl, allyl, propargyl, 2,2,2-trifluoroethyl, methoxy, 2-hydroxyethyl, 2-methoxyethyl, 2-methylthioethyl, 2-aminoethyl, 2-methylaminoethyl, 2-dimethylaminoethyl, 2-acetylaminoethyl, 2-benzoylaminoethyl, methoxycarbonylmethyl, 2-carbamoylpropyl, phenyl, benzyl, heteroraryl, and heteroarylmethyl wherein the heteroaryl part is a furan, thiophene, pyrrole, thiazole, oxazole, imidazole, thiadiazole, oxadiazole, triazole, pyrazole, pyridine or pyrimidine ring and wherein when $R^3$ is or contains a phenyl or heteroaryl ring that ring is optionally substituted by one or two groups selected from fluorine, chlorine, bromine and iodine atoms and methyl, methoxy, methylthio, dimethylamino, acetyl, trifluoromethyl, hydroxy and amino radicals;

$R^4$ is a hydrogen atom, or $R^3$ and $R^4$ are joined to form, together with the nitrogen atom to which they are attached, a pyrrolidine, piperidine, morpholne, piperazine or N-methylpiperazine ring; and the pharmaceutically-acceptable acid-addition salts thereof.

3. A guanidine derivative as claimed in claim 2 in which $R^3$ and $R^4$ are hydrogen atoms.

4. A guanidine derivative as claimed in claim 3 in which $R^2$ is a hydrogen atom and $R^1$ is 2,2,2-trifluoroethyl, 2-chloro-2,2-difluoroethyl or or 2,2,3,3-tetrafluoropropyl radical.

5. A guanidine derivative as claimed in claim 4 in which ring X is a pyrazole, 1,2,3-triazole, 1,2,4-triazole in which A is linked at the 1-position, ring.

6. A guanidine derivative as claimed in claim 5 in which —A— is a tetramethylene, pentamethylene, oxytrimethylene, oxytetramethylene, thiatrimethylene or thiatetramethylene radical.

7. A guanidine derivative selected from the group consisting of 5-[3-(2-[2,2,2-trifluoroethyl]guanidino]-pyrazol-1-yl]valeramide, 5-[3-(2-[2,2,3,3-tetrafluoropropyl]guanidino)pyrazol-1-yl]valeramide, 5-[3-(2-[2-chloro-2,2-difluoroethyl]guanidino)pyrazol-1-yl]valeramide, -[4-(2-[2,2,2-trifluoroethyl]guanidino)-1,2,3-triazol-2-yl]valeramide, 5-[4-(2-[2,2,3,3-tetrafluoropropyl]guanidino)-1,2,3-triazol-2-yl]valeramide, 6-[4-(2-[2,2,2-trifluoroethyl]guanidino)-1,2,3-triazol-2-yl]hexanomide and the pharmaceutically-acceptable acid-addition salts thereof.

8. A pharmaceutical composition which comprises a guanidine derivative as claimed in claim 1 in an amount effective to inhibit gastric acid secretion in a living animal and in association with a pharmaceutically-acceptable diluent or carrier.

9. A method of inhibiting gastric acid secretion in a living animal comprising administering to the animal the composition of claim 8.

* * * * *